(12) United States Patent
Nargund et al.

(10) Patent No.: US 6,294,534 B1
(45) Date of Patent: Sep. 25, 2001

(54) SPIROPIPERIDINE DERIVATIVES AS MELANOCORTIN RECEPTOR AGONISTS

(75) Inventors: Ravi P. Nargund, East Brunswick; Brenda L. Palucki, Belle Mead; Zhixiong Ye, Lawrenceville; Raman K. Bakshi, Edison; Arthur A. Patchett, Westfield; Leonardus H. T. Van Der Ploeg, ScotchPlains, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/329,814

(22) Filed: Jun. 10, 1999

Related U.S. Application Data

(60) Provisional application No. 60/088,908, filed on Jun. 11, 1998, and provisional application No. 60/123,260, filed on Mar. 8, 1999.

(51) Int. Cl.⁷ ........................ A61K 31/44; A61K 31/495; A61K 31/50; C07D 401/04
(52) U.S. Cl. ................... 514/233.5; 514/252.18; 514/253.01; 514/278; 544/124; 544/128; 544/362; 544/363; 544/242; 546/17; 546/18
(58) Field of Search ................ 546/17, 18; 544/124, 544/128, 362, 363, 242; 514/278, 233.5, 252.18, 253.01

(56) References Cited

U.S. PATENT DOCUMENTS

| 5,536,716 | 7/1996 | Chen et al. | 514/215 |
| 5,578,593 | 11/1996 | Chen et al. | 514/212 |
| 5,731,408 | 3/1998 | Hadley et al. | 530/17 |

FOREIGN PATENT DOCUMENTS

| WO 96/05203 | 2/1996 | (WO) . |
| WO 97/34604 | 9/1997 | (WO) . |
| WO 98/10653 | 3/1998 | (WO) . |
| WO 98/25897 | 6/1998 | (WO) . |

OTHER PUBLICATIONS

Life Sciences, vol. 58, No. 20, pp. 1777–1784, 1996, Robert T. Dorr, et als.
The Journal of Urology, vol. 160, 389–393, Aug. 1998, Hunter Wessells, et. als.

*Primary Examiner*—Alan L. Rotman
(74) *Attorney, Agent, or Firm*—Philippe L. Durette; Melvin Winokur; Mollie M. Yang

(57) ABSTRACT

Certain novel spiropiperidine compounds are agonists of melanocortin receptor(s) and are useful for the treatment, control or prevention of diseases and disorders responsive to the activation of melanocortin receptors. The compounds of the present invention are therefore useful for treatment of diseases and disorders such as obesity, diabetes, sexual dysfunction including erectile dysfunction and female sexual dysfunction.

15 Claims, No Drawings

SPIROPIPERIDINE DERIVATIVES AS MELANOCORTIN RECEPTOR AGONISTS

CROSS REFERENCE TO RELATED APPLICATIONS

This application is based on, and claims priority from, provisional applications 60/088,908 filed Jun. 11, 1998, and 60/123,260 filed Mar. 8, 1999, which are hereby incorporated by reference in their entireties.

SUMMARY OF THE INVENTION

Spiropiperidine derivatives are melanocortin receptor agonists, and as such are useful in the treatment of disorders responsive to the activation of melanocortin receptors, such as obesity, diabetes as well as male and/or female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified.

Evidence for the involvement of MC-Rs in obesity includes: i) the agouti ($A^{vy}$) mouse which ectopically expresses an antagonist of the MC-1R, MC-3R and -4R is obese, indicating that blocking the action of these three MC-Rs can lead to hyperphagia and metabolic disorders; ii) MC-4R knockout mice (Huszar et al., Cell, 88, 131–141, 1997) recapitulate the phenotype of the agouti mouse and these mice are obese; iii) the cyclic heptapeptide MT-II (MC-1R, -3R, -4R, -5R, agonist) injected intracerebroventricularly (ICV) in rodents, reduces food intake in several animal feeding models (NPY, ob/ob, agouti, fasted) while ICV injected SHU-9119 (MC-3R, -4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R and -5R and to attenuate food intake and body weight gain over a 12 week period.

Five MC-Rs have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. MC-5R is expressed in many tissues including white fat, placenta and exocrine glands. A low level of expression is also observed in the brain. MC-5R knock out mice reveal reduced sebaceous gland lipid production (Chen et al., Cell, 1997, 91, 789–798).

Intramuscular administration of the MC-1R, -3R, -4R, -5R agonist, melanotan-II (MT-II; 0.005–0.03 mg/kg; Dorr et al., Life Sciences, vol. 58, #20, 1777–1784, 1996) caused intermittent non-painful penile erections in three normal male volunteers for a period of 1–5 hours after dosing. Intramuscular administration of MT-II (0.025 mg/kg and 0.1 mg/kg) to 10 non-organic impotent patients caused transient erections (8 responders) with onset from 50–180 minutes; penile erections subsided after ejaculation (15th American Peptide Symposium Jun. 14–19, 1997, Nashville, Tenn., study now published in J. Urology, 160, 389–393, 1998).

DETAILED DESCRIPTION OF THE INVENTION

The present invention provides compounds having the formula I:

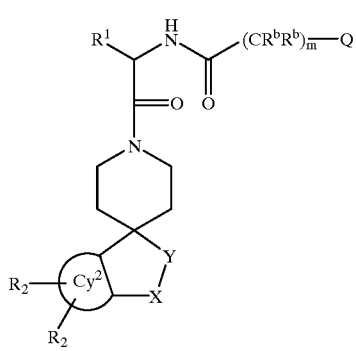

wherein
$Cy^2$ is a six-membered aromatic ring containing 0 or 1N atom or cyclohexane;
Q is

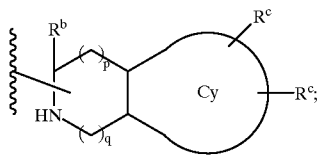

X is O, $CH_2$, $SO_2$, $CHCO_2R^b$, $CHSO_2R^a$, $CHC(O)N(R^b)_2$, $NR^b$, $NSO_2R^a$, $NSO_2N(R^b)_2$, $NCOR^a$, $NCON(R^b)_2$, $CHN(R^b)COR^a$, $CHN(R^b)SO_2R^a$, $CHCH_2OR^b$, or $CH(CH_2)$-heteroaryl;

Y is $(CH_2)_r$, $CH-C_{1-8}$alkyl, O, C=O or $SO_2$, with the proviso that when Y is O, the ring atom of X is carbon;

$R^1$ is H, $C_{1-8}$alkyl, $CH(R^b)$-aryl, $CH(R^b)$-heteroaryl, $(CH_2)_n-C_{5-6}$cycloalkyl in which aryl and heteroaryl are optionally substituted by one or two $R^c$ groups;

$R^2$ is H or halo;

$R^a$ is $R^b$, $(CH_2)_nN(R^b)_2$, $(CH_2)_nN(R^b)C(=NR^d)NR^b$, $(CH_2)_n$NH-2-pyridyl, $(CH_2)_n$NH-2-imidazolyl, $(CH_2)_n$NH-2-thiazolyl, $(CH_2)_n$NH-2-pyrimidinyl,

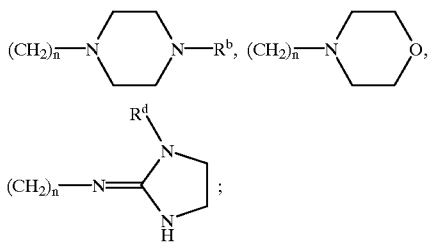

$R^b$ is H, $C_{1-8}$alkyl, $(CH_2)_n$aryl, $(CH_2)_n$heteroaryl, $C_{3-6}$cycloalkyl; or 2 $R^b$ together with the nitrogen atom to which they are attached form a 5- or 6-membered ring optionally containing an additional heteroatom selected from O, S, and $NR^1$;

$R^c$ is $R^b$, halo, $OR^b$, $NHSO_2R^b$, $N(R^b)_2$, CN, $NO_2$, $SO_2N(R^b)_2$, $SO_2R^b$, $CF_3$, $OCF_3$; or two $R^c$ groups attached to adjacent carbon atoms together form methylenedioxy;

$R^d$ is H, $NO_2$, or CN;

Cy is aryl, 5- or 6-membered heteroaryl, 5- or 6-membered heterocyclyl, or 5-or 6-membered carbocyclyl;

n is 0 to 3;

m, p and q are independently 0, 1 or 2;

r is 1, 2 or 3;

or a pharmaceutically acceptable salt thereof.

In one subset of compounds of formula I are compounds wherein $Cy^2$ is benzene or cyclohexane.

In another subset of compounds of formula I are compounds wherein X is $CHCO_2R^b$, $CHC(O)N(R^b)_2$, $NSO_2R^a$, $CHN(R^b)COR^a$, $CHN(R^b)SO_2R^a$, $CHCH_2OR^b$ or $CHCH_2$-heteroaryl.

In another subset of compounds of formula I are compounds wherein Q is

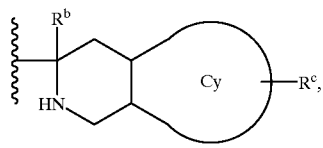

$R^b$ and $R^c$ are as defined under formula I, and Cy is aryl, 5- or 6-membered heteroaryl, or 5- or 6-membered carbocyclyl. Preferably Cy is benzene or cyclohexane.

In another subset of compounds of formula I are compounds wherein $R^1$ is $CH_2$-aryl in which aryl is optionally substituted by $R^c$.

In a preferred embodiment there are provided compounds of formula Ia:

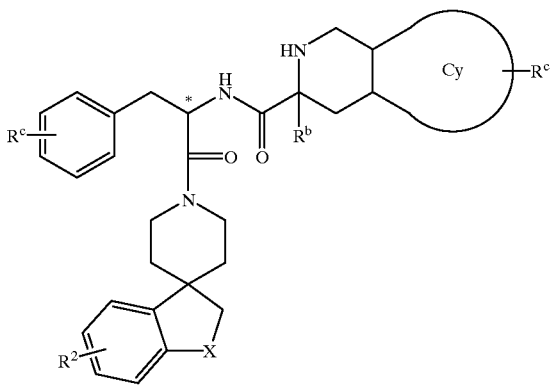

Ia wherein

X is $CHCO_2R^b$, $CHC(O)N(R^b)_2$, $NSO_2R^a$, $CHN(R^b)COR^a$, or $CHN(R^b)SO_2R^a$;

$R^2$ is H or halo;

$R^a$ is $R^b$, $(CH_2)_nN(R^b)_2$, $(CH_2)_n$NH-2-pyridyl, $(CH_2)_n$NH-2-imidazolyl, $(CH_2)_n$NH-2-thiazolyl, $(CH_2)_n$NH-2-pyrimidinyl,

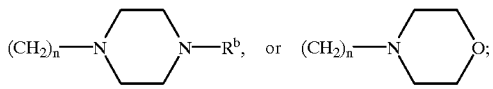

$R^b$ is H, $C_{1-8}$alkyl, $(CH_2)_n$aryl, $(CH_2)_n$heteroaryl, or $C_{3-6}$cycloalkyl;

$R^c$ is H, halo, $R^b$, $OR^b$, $CF_3$, $OCF_3$;

Cy is benzene, pyridine, imidazole or cyclohexane;

n is 0 to 3;

or a pharmaceutically acceptable salt thereof.

In another preferred embodiment are compounds of the formula Ib:

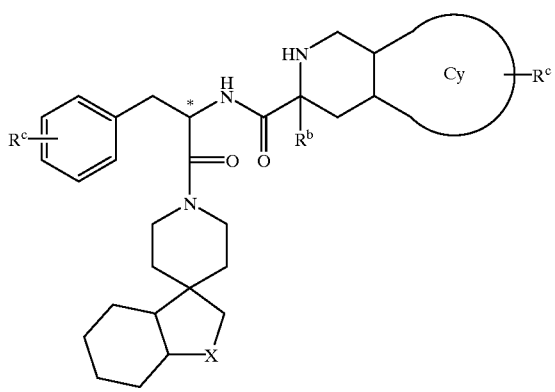

Ib wherein

X is $CHCO_2R^b$, $CHC(O)N(R^b)_2$, $CHCH_2OR^b$ or $CHCH_2$-heteroaryl;

$R^b$ is H, $C_{1-8}$alkyl, $(CH_2)_n$aryl, $(CH_2)_n$heteroaryl, or $C_{3-6}$cycloalkyl;

$R^c$ is H, halo, $R^b$, $OR^b$, $CF_3$, $OCF_3$;

Cy is benzene, pyridine, imidazole or cyclohexane;

n is 0 to 3;

or a pharmaceutically acceptable salt thereof.

In a more preferred embodiment of compounds of formulas Ia and Ib, the carbon atom marked with * has the R configuration. In another more preferred embodiment of formulas Ia and Ib Cy is benzene or cyclohexane.

Representative compounds of formula I are as follows:

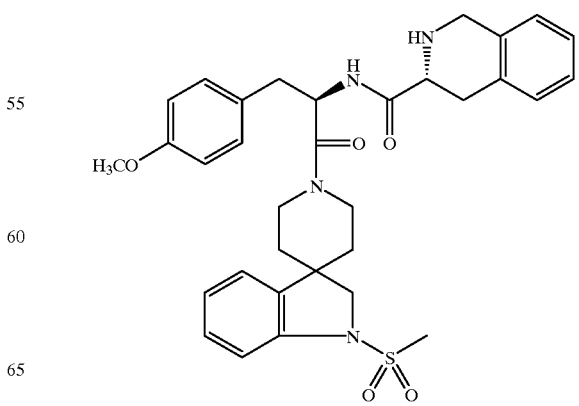

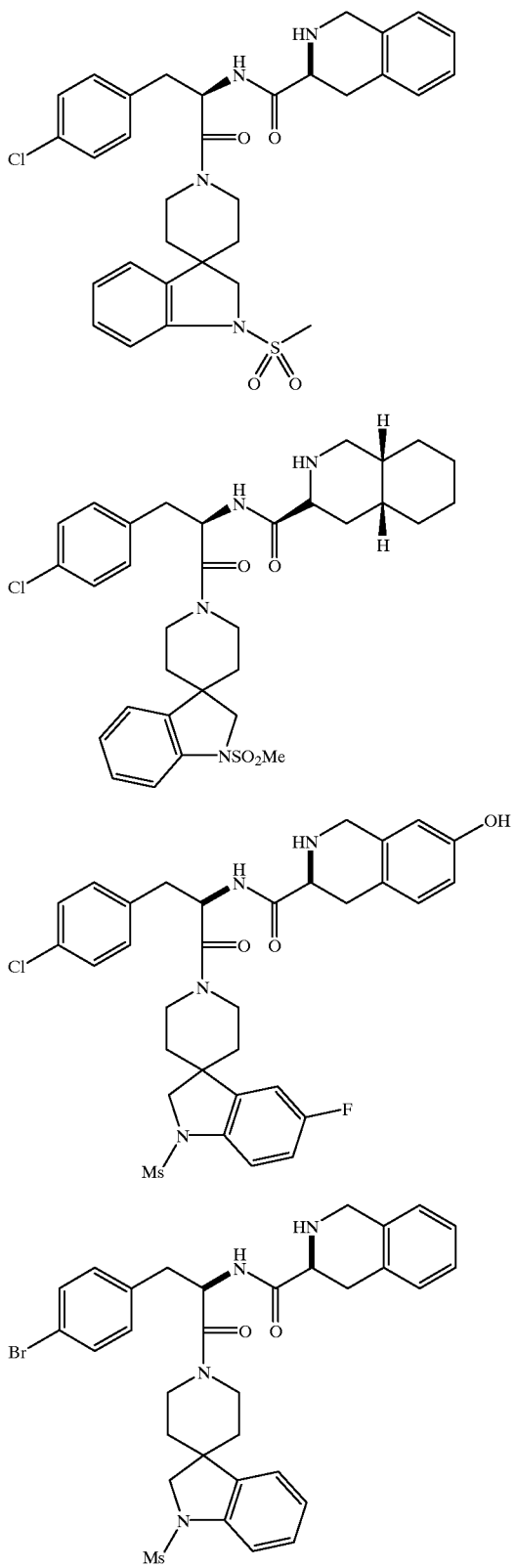
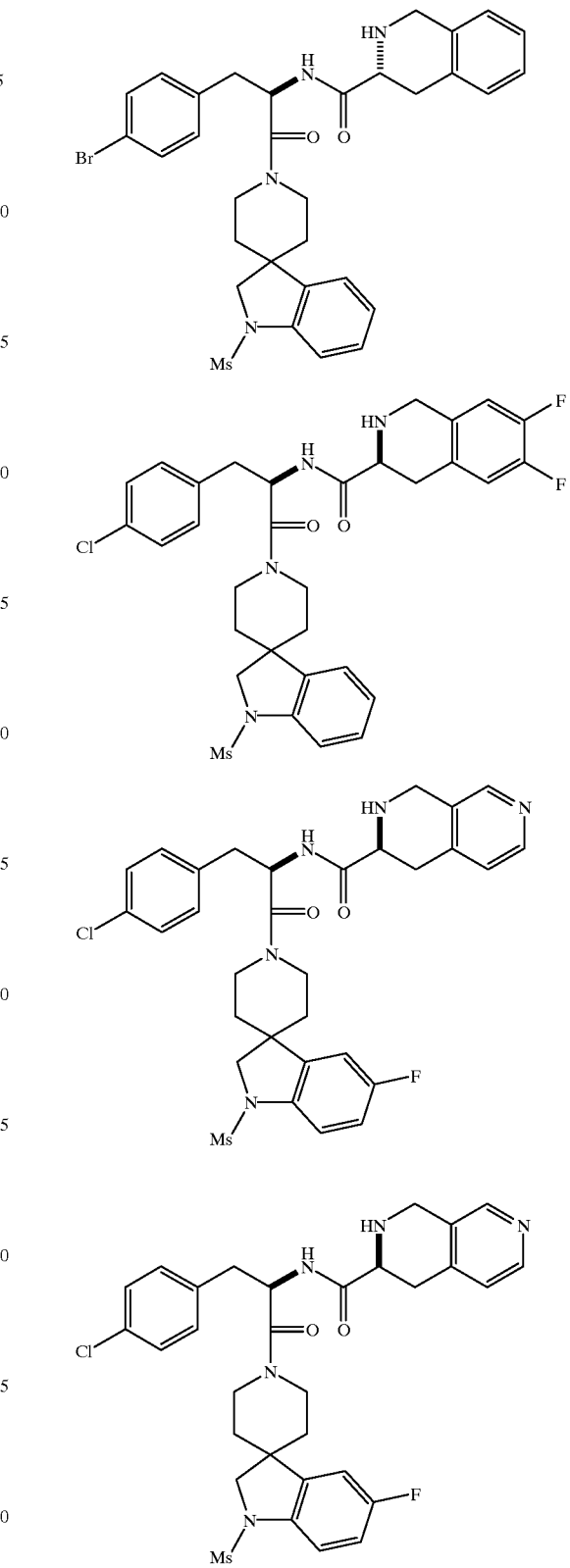

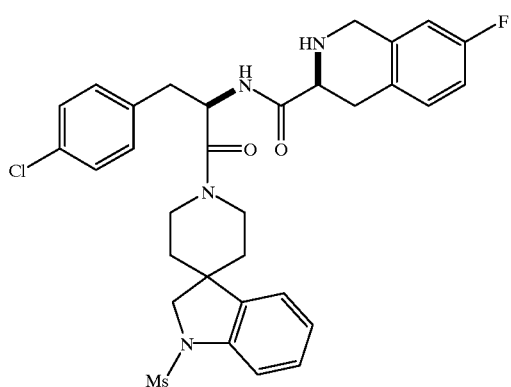
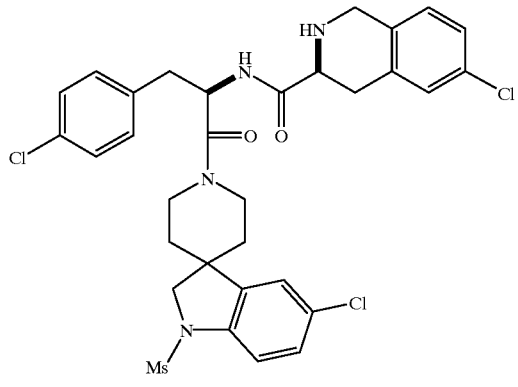

-continued

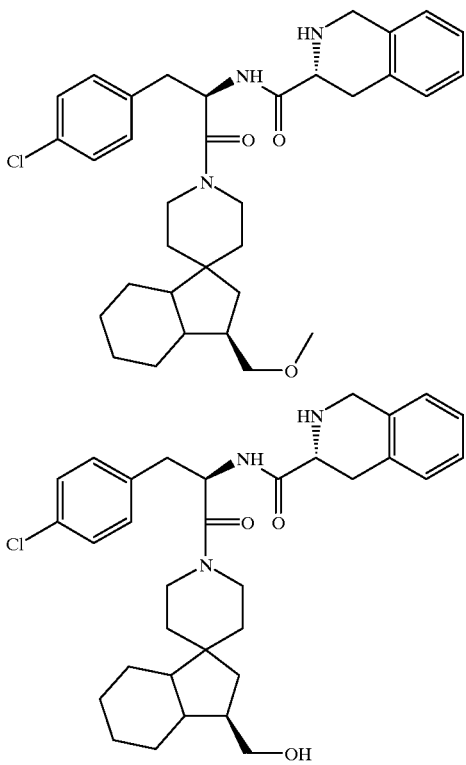

Another aspect of the present invention provides a method for the treatment or prevention of obesity or diabetes in a mammal which comprises administering to said mammal an effective amount of a compound of formula I.

Another aspect of the present invention provides a method for the treatment or prevention of male or female sexual dysfunction including erectile dysfunction which comprises administering to a patient in need of such treatment or prevention an effective amount of a compound of formula I.

Another aspect of the present invention provides a method for the treatment or prevention of male or female sexual dysfunction including erectile dysfunction which comprises administering to a patient in need of such treatment or prevention an effective amount of an agonist of melanocortin-4 receptor.

Yet another aspect of the present invention provides a pharmaceutical composition comprising a compound of formula I and a pharmaceutically acceptable carrier.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" are monocyclic heteroaromatic rings, examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^bR^b$ may represent $NH_2$, $NHCH_3$, $N(CH_3)CH_2CH_3$, and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, inability to achieve an orgasm. An increase in erectile dysfunction is often associated with age and is generally caused by a physical disease or as a side-effect of drug treatment.

"Female sexual dysfunction" encompasses, without limitatin, conditions usch as a lack of sexual desire and related arousal disorders, inhibited orgasm, lubrication difficulties, and vaginismus.

| Abbreviations Used | |
|---|---|
| 9-BBN | 9-borabicyclo[3.3.1]nonane |
| Bn | benzyl |
| BOC (boc) | t-butyloxycarbonyl |
| BOP | benzotriazol-1-yloxy tris(dimethylamino)phosphonium hexafluorophosphate |
| Bu | butyl |
| calc. | calculated |
| CBZ (Cbz) | benzyloxycarbonyl |
| DCC | dicyclohexylcarbodiimide |
| DCM | dichloromethane |
| DIEA | diisopropylethylamine |
| DMAP | 4-(N,N-dimethylamino)pyridine |
| DMF | dimethylformamide |
| DPPA | diphenylphosphoryl azide |
| EDC | 1-(3-dimethylaminopropyl)3-ethylcarbodiimide HCl |
| eq. | equivalent(s) |
| ESI-MS | electron ion-mass spectroscopy |
| EtOAc | ethyl acetate |
| FAB-MS | fast atom bombardment-mass spectroscopy |
| HOBt | 1-hydroxybenzotriazole hydrate |
| HPLC | high pressure liquid chromatography |
| KHDMS | potassium bis(trimethylsilyl)amide |
| LAH | lithium aluminum hydride |
| LHMDS | lithium bis(trimethylsilyl)amide |

-continued

Abbreviations Used

| | |
|---|---|
| MC-xR | melanocortin receptor (x being a number) |
| Me | methyl |
| MF | molecular formula |
| MHz | megahertz |
| MPLC | medium pressure liquid chromatography |
| Ms | methanesulfonyl |
| NMM | N-methylmorpholine |
| NMR | nuclear magnetic resonance |
| PCC | pyridium chlorochromate |
| Ph | phenyl |
| Pr | propyl |
| prep. | prepared |
| PyBrop | bromo-tris-pyrrolidino-phosphonium hexafluorophosphate |
| TFA | trifluoroacetic acid |
| THF | tetrahydrofuran |
| Tic | 1,2,3,4-tetrahydroisoquinoline-3-carboxylic acid |
| TLC | thin-layer chromatography |
| TMS | tetramethylsilane |

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immune modulation, rheumatoid arthritis, skin tanning, acne and other skin disorders, neuroprotective and cognitive and memory enhancement including the treatment of Alzheimer's disease. Some compounds of formula I show highly specific activity toward the melanocortin-4 receptor which makes them especially useful in the prevention and treatment of obesity, as well as male and female sexual dysfunction.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists such as those disclosed in WO97/28149;

(g) antiobesity compounds such as fenfluramine, dexfenfluramine, phentermine, sibutramine, orlistat, or $β_3$ adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677; and (m) agents useful in the treatment of male and/or female sexual dysfunction such as phosphodiester V inhibitors such as sildenafil, and α-2 adrenergic receptor antagonists.

Biological Assays

A. Binding Assay. The membrane binding assay is used to identify competitive inhibitors of $^{125}$I-α-NDP-MSH binding to cloned human MCRs expressed in L- or CHO- cells.

Cell lines expressing melanocortin receptors are grown in T-180 flasks containing selective medium of the compositon: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 ml 10,000 unit/ml penicillin & 10,000 ug/ml streptomycin (Gibco/BR1); 10 ml 200 mM L-glutamine (Gibco/BR1); 1 mg/ml Geneticin (G418) (Gibco/BR1). The cells are grown at 37° C. with $CO_2$ and humidity control until the desired cell density and cell number is obtained The medium is poured off and 10 mls/monolayer of enzyme-free dissociation media (Specialty Media Inc.) is added. The cells are incubated at 37° C. for 10 minutes or until cells slough off when flask is banged against hand.

The cells are harvested into 200 ml centrifuge tubes and spun at 1000 rpm, 4° C., for 10 min. The supernatant is discarded and the cells are resuspended in 5 mls/monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells are homogenized with motor-driven dounce (Talboy setting 40), using 10 strokes and the homogenate centrifuged at 6,000 rpm, 4 C, for 15 minutes.

The pellets are resuspended in 0.2 mls/monolayer membrane prep buffer and aliquots are placed in tubes (500–1000 ul/tube) and quick frozen in liquid nitrogen and then store at −80° C.

Test compounds or unlabelled NDP-α-MSH is added to 100 $μL$ of membrane binding buffer to a final concentration of 1 $μM$. The membrane binding buffer has the composition: 50 mM Tris pH 7.2; 2 mM $CaCl_2$; 1 mM $MgCl_2$; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred $μl$ of membrane binding buffer containing 10–40 ug membrane protein is added, followed by 100 $μM$ 125I -NDP-α-MSH to final concentration of 100 pM. The resulting mixture is vortexed briefly and incubated for 90–120 min at room temp while shaking.

The mixture is filtered with Packard Microplate 196 filter apparatus using Packard Unifilter 96-well GF/C filter with 0.1% polyethyleneimine (Sigma). The filter is washed (5 times with a total of 10 ml per well) with room temperature of filter wash having the composition: 50 mM Tris-HCl pH 7.2 and 20 mM NaCl. The filter is dried, and the bottom sealed and 50 ul of Packard Microscint-20 is added to each well. The top is sealed and the radioactivity quantitated in a Packard Topcount Microplate Scintillation counter.

B. Functional Assay. Functional cell based assays are developed to discriminate agonists and antagonists.

Cells (for example, CHO- or L-cells or other eukaryotic cells) expressing a human melanocortin receptor (see e.g. Yang-YK; Ollmann-MM; Wilson-BD; Dickinson-C; Yamada-T; Barsh-GS; Gantz-I; Mol-Endocrinol. 1997 Mar; 11(3): 274–80) are dissociated from tissue culture flasks by rinsing with Ca and Mg free phosphate buffered saline (14190-136, Life Technologies, Gaithersburg, Md.) and detached following 5 minutes incubation at 37° C. with enzyme free dissociation buffer (S-014-B, Specialty Media, Lavellette, N.J.). Cells are collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells are counted and diluted to 1 to $5×10^6$/ml. The phosphodiesterase inhibitor 3-isobutyl-1-methylxanthine is added to cells to 0.6 mM.

Test compounds are diluted in dimethylsulfoxide (DMSO) ($10^{-5}$ to $10^{-10}$M) and 0.1 volume of compound solution is added to 0.9 volumes of cell suspension; the final DMSO concentration is 1%. After room temperature incubation for 45 min., cells are lysed by incubation at 100 C for 5 min. to release accumulated cAMP.

cAMP is measured in an aliquot of the cell lysate with the Amersham (Arlington Heights, Ill.) cAMP detection assay (RPA556). The amount of cAMP production which results from an unknown compound is compared to that amount of cAMP produced in response to alpha-MSH which is defined as a 100% agonist. The $EC_{50}$ is defined as the compound concentration which results in half maximal stimulation, when compared to its own maxim level of stimulation.

Antagonist assay: Antagonist activity is defined as the ability of a compound to block cAMP production in response to alpha-MSH. Solution of test compounds and suspension of receptor containing cells are prepared and mixed as described above; the mixture is incubated for 15 min., and an EC50 dose (approximately 10 nM alpha-MSH) is added to the cells. The assay is terminated at 45 min. and cAMP quantitated as above. Percent inhibition is determined by comparing the amount of cAMP produced in the presence to that produced in the absence of test compound.

C. In Vivo Food Intake Models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

a) Conditioning to Supine Restraint for Ex Copula Reflex Tests. This conditioning takes~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

b) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunctioin

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna KE et al, A Model For The Study Of Sexual Function In Anesthetized Male And Female Rats, Am. J. Physiol. (Regulatory Integrative Comp. Physiol 30): R1276–R1285, 1991; McKenna KE et al, Modulation By Peripheral Serotonin Of The Threshold For Sexual Reflexes In Female Rats, Pharm. Bioch. Behav., 40:151–156, 1991; and Takahashi L K et al, Dual Estradiol Action In The Diencephalon And The Regulation Of Sociosexual Behavior In Female Golden Hamsters, Brain Res., 359:194–207, 1985.

Preparation of Compound of the Invention

The preparation of compounds of Formula I of the present invention may be carried out in sequential or convergent synthetic routes. Syntheses detailing the preparation of the compounds of Formula I in a sequential manner are presented in the following reaction schemes. The instant compounds are generally isolated in the form of their pharmaceutically acceptable salts, such as those described previously hereinabove.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC are used extensively in the synthesis, and their removal conditions are known to those skilled in the art. For example, removal of CBZ groups can be achieved by a number of methods known in the art; for example, catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Activeα-Amino Acids*, Pergamon Press: Oxford, 1989). Many of the piperidines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures include crystallization, normal phase or reverse phase chromatography.

Intermediates of Formula 3 may be synthesized as described in Scheme 1. Coupling of amine of Formula 2 to protected amino acids of Formula 1, wherein L is a suitable protecting group (BOC, CBZ, etc), is conveniently carried out under standard peptide coupling conditions, and the removal of the protecting group may be conducted using well-known methods.

Compounds of Formula I may be prepared as shown in Schemes 2 and 3. In Scheme 2 intermediates of Formula 3 are coupled to protected amino acids of Formula 4 (L=protecting group such as Boc, CBZ, FMOC, etc.) under the standard peptide-type coupling reaction conditions. The amino acids 4 are either commercially available or can be synthesized by methods as described later.

In Scheme 3, amino acid ester intermediates of Formula 5, wherein L' is a small alkyl such as methyl or ethyl or a benzyl or allyl unit, can be synthesized by well documented methods in the literature. Coupling of intermediates 4 and 5 under standard peptide coupling conditions followed by removal of the ester group L' yields the intermediate 6. Compounds of formula I are obtained by coupling intermediates of Formula 6 to spiropiperidines of formula 2 under standard peptide coupling reaction conditions, followed by the removal of the amino protecting group, L.

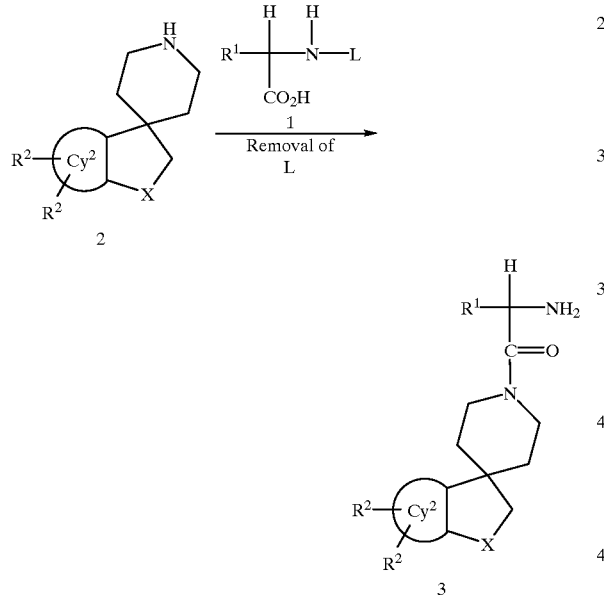

-continued

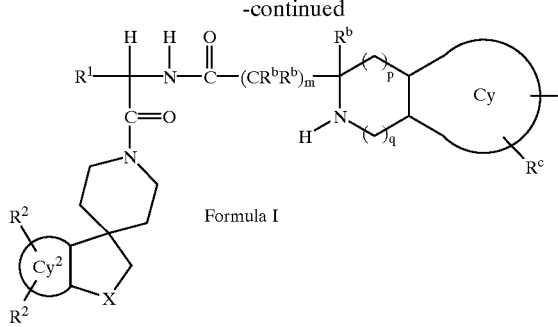

Formula I

The compounds of the present invention may also be prepared from a variety of substituted natural and unnatural amino acids of formulas 8.

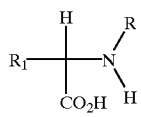

8

The preparation of many of these acids is described in U.S. Pat. No. 5,206,237. The preparation of these intermediates in racemic form is accomplished by classical methods familiar to those skilled in the art (Williams, R. M. *"Synthesis of Optically Active α-Amino Acids"* Pergamon Press: Oxford, 1989; Vol. 7). Several methods exist to resolve (DL)-amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives (*"Asymmetric Synthesis, Chiral Catalysis"*; Morrison, J. D., Ed; Academic Press: Orlando, Fla., 1985; Vol 5), and (6) enzymatic syntheses (*Angew. Chem. Int. Ed. Engl.* 1978, 17, 176).

SCHEME 4

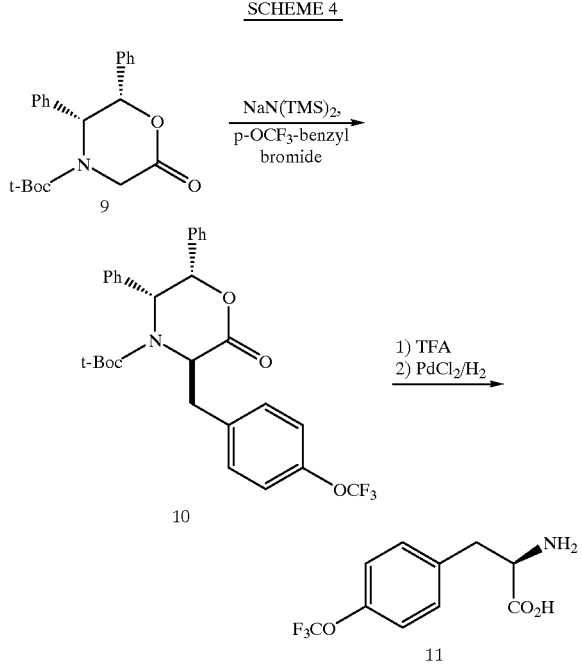

For example, alkylation of the enolate of diphenyloxazinone 9 (*J. Am. Chem. Soc.* 1991, 113, 9276) with p-trifluoromethoxybenzyl bromide in the presence of sodium bis(trimethylsilyl)amide proceeds smoothly to afford 10 which is converted into the desired (D)-amino acid 11 by removing the N-t-butyloxycarbonyl group with trifluoroacetic acid and hydrogenation over a $PdCl_2$ catalyst (Scheme 5).

The spiropiperidines of formula 12 may be prepared by a number of methods, including the syntheses described below. In cases where a sulfide is present in the molecule, it may be oxidized to a sulfoxide or to a sulfone with oxidizing agents such as sodium periodate, m-chloroperbenzoic acid or Oxone " in an solvent such as dichloromethane, alcohol or water or their mixtures.

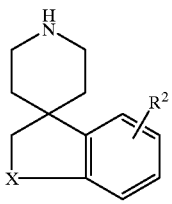

X = $NR^b$, $NSO_2R^a$, $NSO_2N(R^b)_2$, $NCOR^a$, $NCON(R^b)_2$

As shown in Scheme 5, the spiropiperidine of formula 13, wherein L is a protecting group (such as methyl or benzyl), is synthesized by methods that are known in the literature (for example H. Ong et al *J. Med. Chem.* 1983, 23, 981–986). The indoline nitrogen of 13 can be reacted by with a variety of electrophiles to yield spiro piperidines of formula 14, wherein the substitutent can be a variety of functionalities, including $R^b$, $SO_2R^a$, $SO_2N(R^b)_2$, $COR^a$, $CON(R^b)_2$. Compound 13 can be reacted with, for example, isocyanates in an inert solvent like dichloromethane to yield urea derivatives, chloroformates in an inert solvent such as dichloromethane to yield carbamates, acid chlorides, anhydrides, or acyl imidazoles to generate amides, sulfonyl chlorides to generate sulfonamides, sulfamyl chlorides to yield sulfamides.

Also, the indoline nitrogen of 13 can be reductively alkylated with aldehydes with conditions known in the art. Aromatic units, including substituted heteroaryl groups, can be introduced by reacting 13 with a fluoro phenyl or fluoro heteroaryl reagent. This chemistry is detailed by H. Ong et al *J. Med. Chem.* 1983, 23, 981–986.

SCHEME 5

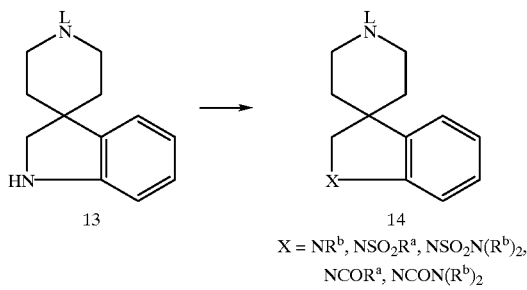

X = NR$^b$, NSO$_2$R$^a$, NSO$_2$N(R$^b$)$_2$, NCOR$^a$, NCON(R$^b$)$_2$

As shown in Scheme 6, the spiro piperidine intermediate 14 (L=Me or Bn) can be demethylated or debenzylated using a number of methods well know to those skilled in the art to produce 15. Demethylation of 14 be accomplished by reacting it with cyanogen bromide and potassium carbonate in an inert solvent such as dichloromethane to yield a cyanamide which can reduced to give 15 by treatment with lithium aluminum hydride in refluxing tetrahydrofuran, refluxing strong acid like aqueous hydrochloric acid, or with Grignard reagents like methyl magnesium bromide. Alternatively, demethylation of 14 can be effected with the ACE-Cl method as described in R. Olofson et al. *J. Org. Chem.* 1984, 49, 2795 and references therein. Debenzylation can be accomplished by reductive methods including hydrogenation in the presence of platinum or palladium catalyst in a protic solvent like methanol. Alternatively, debenzylation of 14 can be effected with the ACE-Cl method as described in R. Olofson et al. *J. Org. Chem.* 1984, 49, 2795 and references therein.

SCHEME 6

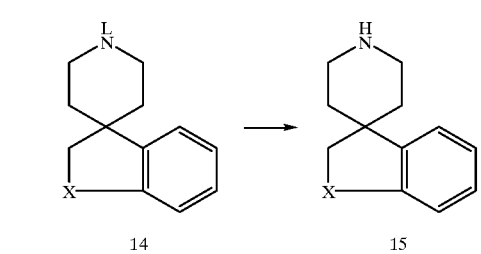

L = methyl or benzyl
X = NR$^b$, NSO$_2$R$^a$, NSO$_2$N(R$^b$)$_2$, NCOR$^a$, NCON(R$^b$)$_2$ The spiro heterocyclic compounds of formula 15 can be prepared by a number of methods, including the syntheses as described in Scheme 7. Allylic oxidation of the protected piperidine 17 is accomplished by classical methods familiar to those skilled in the art (Rabjohn, N. *Org. React.* 1976, 24, 261). The resulting allylic alcohol is treated with thionyl chloride in an inert solvent such as benzene to provide the corresponding chloride 18. When X=O or S, the alkylation is carried out in DMF or acetone as solvent with potassium carbonate as a base, and when X=N or derivativized with an alkyl, aryl, acyl, sulfonyl, carbamate) the reaction is carried out with sodium hydride as a base in an inert solvent such as THF to afford the cyclization precursor 19. When L is a defined protecting group, compound 19 can be cyclized by a number methods familiar to those skilled in the art. For example, cyclization of 19 can be accomplished by reaction with tributyltin hydride (Curran, D. P. *Synthesis* 1988, 417 and 489) in an inert solvent such as benzene to yield 16.

SCHEME 7

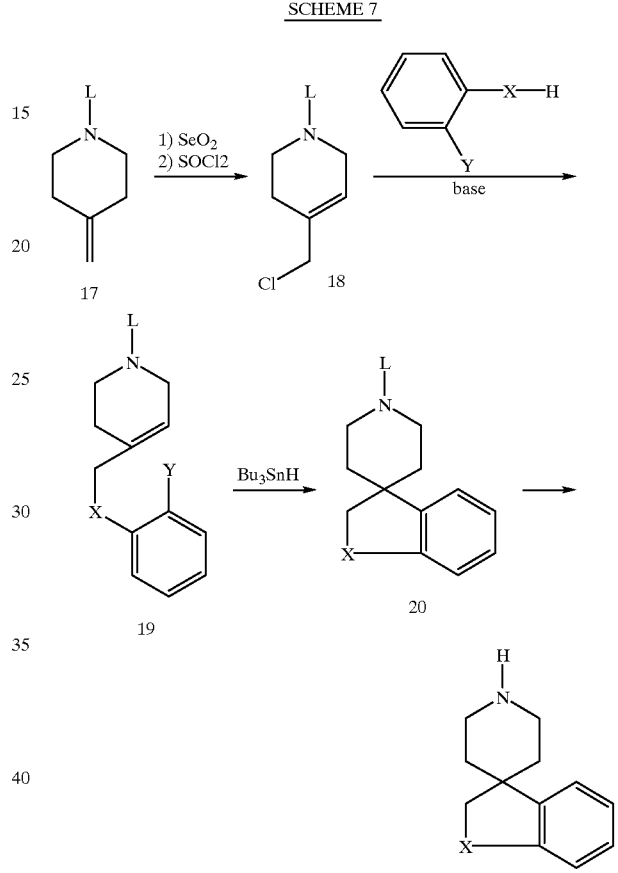

X = NR$^b$, NSO$_2$R$^a$, NSO$_2$N(R$^b$)$_2$, NCOR$^a$, NCON(R$^b$)$_2$
Y = halide, Se or S

SCHEME 8

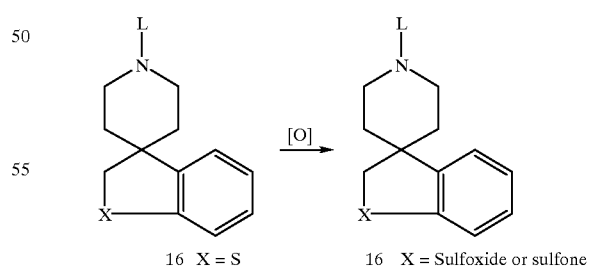

16  X = S          16  X = Sulfoxide or sulfone

As shown in Scheme 8, when X=S, compound 16 can be oxidized to the sulfoxide 16 (X=S(O)) and the sulfone 16 (SO2) by many oxidizing agents. For example, sodium periodate is often used for the synthesis of sulfoxides and Oxone is used for the synthesis of sulfones. Removal of the protecting group provides the amine 16 which then can be elaborated to melanocortin agonists.

SCHEME 10

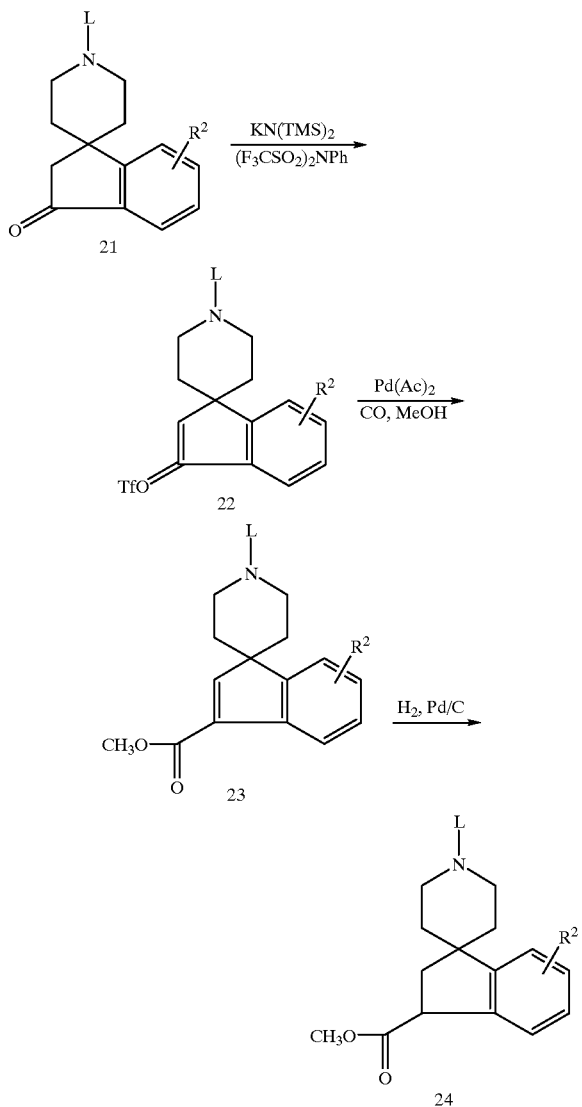

Homologation of the spiroindanone 21 provides easy access to spiroindanyl intermediates containing acid and ester groups. This chemistry is described in Scheme 10. Treatment of 21 with a base in an inert solvent such as THF followed by the addition of a triflating agent provides the enol triflate. Carboxylation of the enol triflate according to the procedure of Cacchi, S. *Tetrahedron Letters*, 1985, 1109–1112 provides the ester 23. Hydrogenation of 23 using a palladium catalyst in an inert solvent provides the saturated ester 24. The protecting group can then be removed as described above and the resulting amine can be incorporated into the subject compound via the chemistry depicted in earlier schemes.

Saponification of the ester of 24 provides an acid which can be conveniently derivatized as for example reaction with an amine in the presence of a coupling agent such as EDC gives amides which can then be incorporated into final compounds.

The ester 24 may also be reduced to a primary alcohol with LAH and to a aldehyde with DIBALH. Reductive alkylation of the aldehyde with ammonium acetate and sodium cyanoborohydride affords an amino methyl analog. These aminomethyl analogs may then be further reacted with acylating and sulfonylating agents to afford additional melanocortin compounds of the general formula I.

As illustrated in Scheme 11, spiroindanes can be hydrogenated with Pt/C or Rh/alumina as catalysts in solvents such as methanol, ethanol or acetic acid to afford corresponding perhydroindanes. High pressures are often required to carry out this saturation reaction. The L protecting group can be removed by standard methods as discussed above.

SCHEME 11

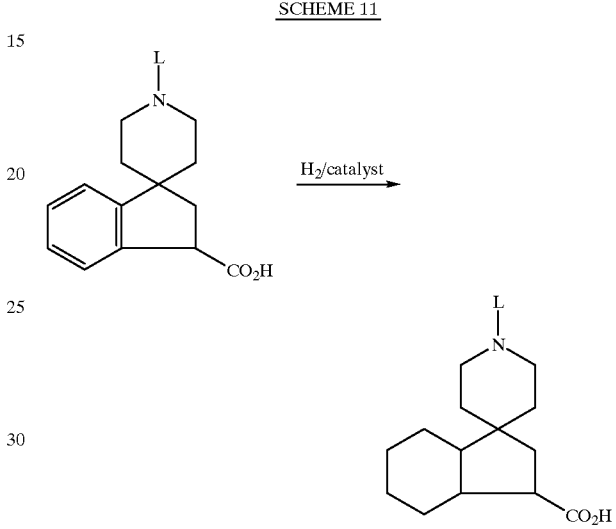

Chiral acids are available by a variety of methods known to those skilled in the art including asymmetric catalytic hydrogenation and resolution of a pair of diastereomeric salts formed by reaction with a chiral amine such as D or L α-methylbenzylamine. The absolute stereochemistry can be determined in a number of ways including X-ray crystallography of a suitable crystalline derivative.

Protected amino acids of formula 5, wherein L is a suitable protecting group such as Boc or CBZ, can by conveniently synthesized by methods well documented in the literature.

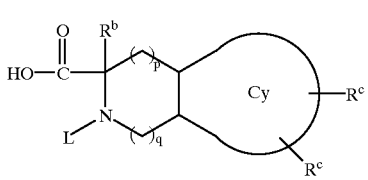

For example, as shown in Scheme 11, a substituted phenyl alanine derivative 25 can be treated with aqueous formaldehyde in concentrated hydrochloric acid to afford, after protection of the amino functionality in a second step by well documented methods, the tetrahydroisoquinoline compound 26. This reaction can also be effected with heterocyclic amino acids such as 2- and 3-thienyl Ala. Since the above chemistry works generally with retention of stereochemistry, D- and L-amino acids of general formula 5 can be prepared from D- and L-amino acids.

SCHEME 12

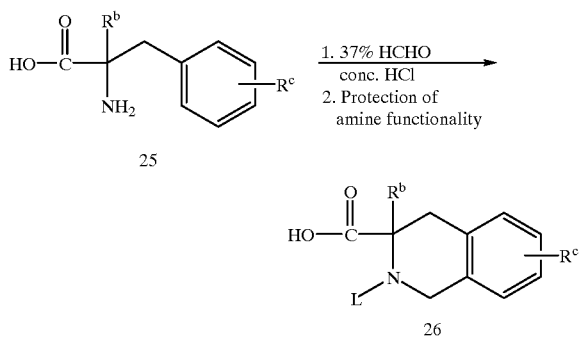

As shown in Scheme 12, a second method to prepare compounds of formula 5 includes alkylation of a dihalide (L=Br, Cl, I) of formula 27 with dimethylacetamidomalonate in the presence of a strong base such as NaH in DMF to afford alkylated material of formula 28. Treatment of esters of formula 28 with alkali leads to formation of the corresponding mono carboxylic acid which can be treated with refluxing hydrochloric to affect hydrolysis of the acetamide derivative to provide amino acid of formula 29. Once again, standard protection of the amino functionality provides intermediates of formula 30.

SCHEME 13

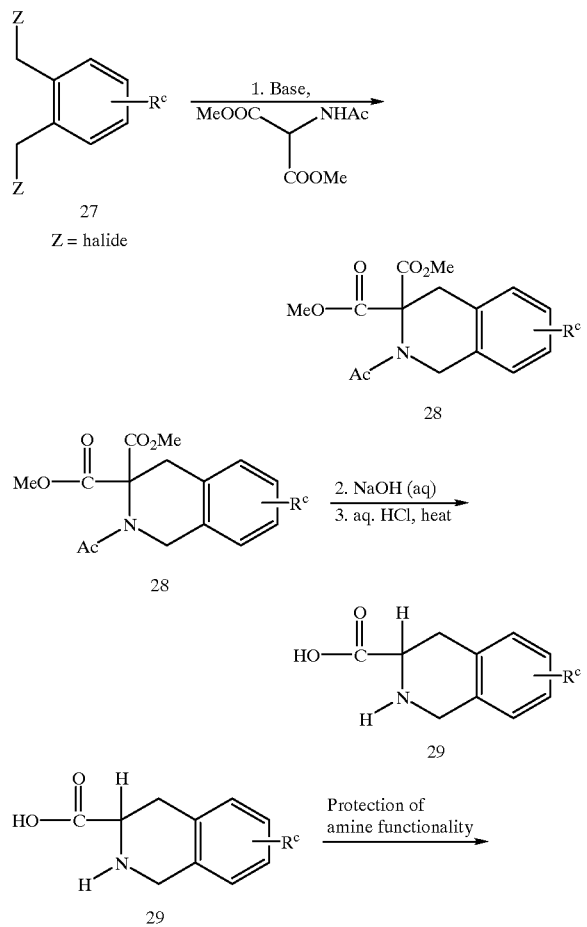

-continued

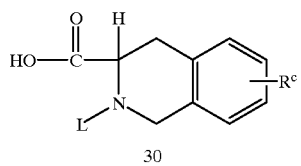

Saturated amino side chains of formula 31 can be prepared by hydrogenating compounds of formula 30 in the presence of rhodium or platinum catalysts.

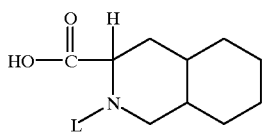

For example, following the method of Ornstein and coworkers (Ornstein, P. L.; Arnold, M. B.; Augenstein, N. K.; Paschal, J. W. *J. Org Chem.* 1991, 56, 4388), compound 30 can be hydrogenated in the presence of 5% Rh on alumina to give compound 31. Individual diastereomers of 31 can be resolved via classical resolution methods.

Schemes 14 illustrates one method for the preparation of tetrahydroisoquinolineacetic acid of formula 33. This is carried out conveniently by the Arndt-Eistert reaction which proceeds with retention of stereochemistry. Other methods involve require reduction of the acid or its ester derivative to an alcohol, conversion of the alcohol to a leaving group such as a mesylate or halide, displacement of it with cyanide anion and hydrolysis of the nitrile to the carboxylic acid by well documented literature methods.

SCHEME 14

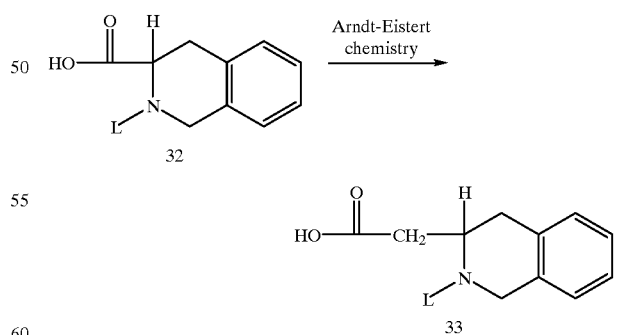

It is understood that in some cases the order of carrying out the foregoing reaction schemes may be varied to facilitate the reaction or to avoid unwanted reaction products.

PREPARATION OF INTERMEDIATES

INTERMEDIATE 1

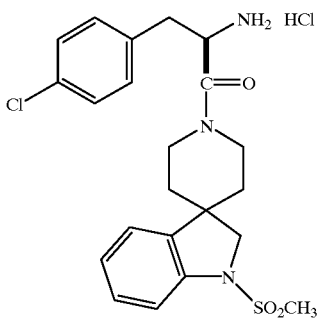

To a solution of N-Boc-D-4-chlorophenylalanine (10.95 g; 36.55 mmol) in 166 mL of dichloromethane was added 10.06 g (33.27 mmol) of 1,2-dihydro-1-methanesulfonylspiro[3H-indole-3,4'-piperidine] hydrochloride (see for example U.S. Pat. No. 5,536,716), 11 mL of N-methylmorpholine, 7.01 g of EDC and 4.94 g of HOBt and stirred at room temperature for 18 h. The reaction mixture was diluted with dichloromethane and washed with 1N HCl and saturated aqueous sodium bicarbonate solution and brine. The organic layer was dried over MgSO$_4$ and evaporated to give an intermediate that was chromatographed on silica gel using hexane-ethyl acetate (1:1) as the eluent to give the coupled product.

The product above was dissolved in 140 mL of dichloromethane and treated with 25 mL of 4.0M HCl in dioxane for 18 h. The volatiles were removed and the sticky residue was dissolved in methanol and concentrated to dryness to provide the desired title compound.

$^1$H NMR (CD$_3$OD, 400MHz) 7.26–7.12 (m, 5 H); 4.90–4.37 (m, 1 H); 2.65–2.60 (m, 2 H); 1.97 (s, 3 H); 1.87–1.82 (m, 1 H); 1.73–1.65 (m, 3 H).

INTERMEDIATE 2–5

The following Intermediates were prepared from the appropriately substituted phenylalanine (Phe) and spiroindoline in an analogous manner to the one described for the preparation of Intermediate 1.

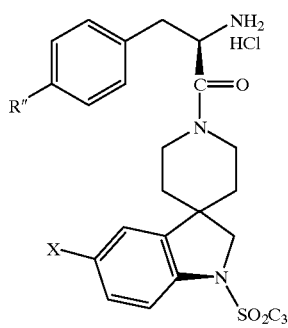

| Intermediate | Phe | R" | x |
|---|---|---|---|
| 2 | N-Boc-D-4-methoxy-Phe | CH$_3$O | H |
| 3 | N-Boc-D-4-bromo-Phe | Br | H |

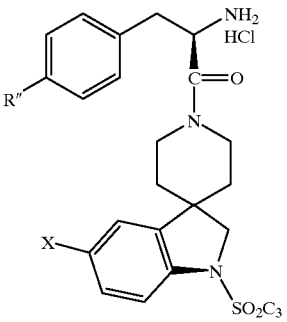

| Intermediate | Phe | R" | x |
|---|---|---|---|
| 4 | N-Boc-D-4-chloro-Phe | Cl | F* |
| 5 | N-Boc-D-4-methyl-Phe | CH$_3$ | H |

*the starting material, 1,2-dihydro-5-fluoro-1-methanesulfonylspiro[3H-indole-3,4'-piperidine]hydrochloride, may be prepared according to general method disclosed in U.S. Pat. No. 5536716.

INTERMEDIATE 6

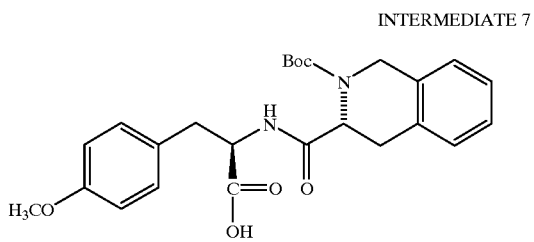

To a solution of of D-4-chlorophenylalanine methyl ester ochloride in dichloromethane was added N-Boc-D-1,2,3,4-tetrahydroquinoline-3-carboxylic acid (N-Boc-D-Tic), EDC, HOBT and NMM, and the mixture was stirred at room temperature overnight. The crude product was isolated after standard workup as described for the preparation of Intermediate 1. The crude ester was dissolved in methanol-water (1:1) and hydrolyzed to the desired acid by treatment with 2.5 eq. of NaOH. The reaction mixture was concentrated to ~50% of the volume, acidified to pH 2 with 1N HCl and extracted with dichloromethane. The combined organics were washed with brine, dried over anhydrous magnesium sulfate, filtered and concentrated to give the desired product as a colorless solid.

INTERMEDIATE 7

The title compound was synthesized in an analogous manner to Intermediate 3 using D-4-(methoxy)phenylalanine methyl ester hydrochloride in place of D-4-chlorophenylalanine methyl ester hydrochloride.

INTERMEDIATE 8

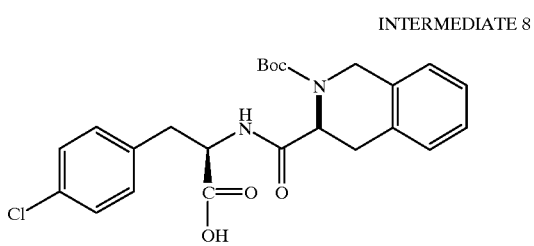

The title compound was synthesized in an analogous manner to Intermediate 3 using N-Boc-L-Tic in place of N-Boc-D-Tic.

INTERMEDIATE 9

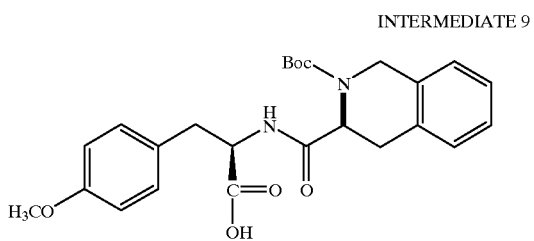

The title compound was synthesized in an analogous manner to Intermediate 4 using t N-Boc-L-Tic in place of N-Boc-D-Tic.

INTERMEDIATE 10

3R-3-amino-1'-(t-butyloxycarbonyl)spiro[1H-indan-1,4'-piperidine]

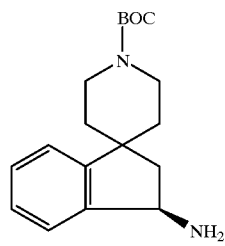

Step A: Preparation of 3-oxo-1'-(t-butyloxycarbonyl)spiro[1H-indan-1,4'-piperidine]

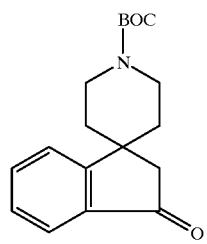

To a solution of 51.0 g (0.177 mol) of 1'-(t-butyloxycarbonyl)spiro[1H-indene-1,4'-piperidine] [prepared by the method of Chambers, et al, *J. Med. Chem.*, 1992, 35, 2036] in 200 ml of THF was added 430 ml (0.5M in THF, 0.213 mol) of 9-BBN. The reaction mixture was heated at 70° C. until TLC analysis indicated that the starting material was consumed (18 hrs). The solution was concentrated to ~300 ml and then cooled to 0° C. and quenched with methanol (10 ml). 4N Sodium hydroxide (213 ml) and 30% hydrogen peroxide (108 ml) were added via an addition funnel over 45 minutes. The reaction mixture was stirred for 3.5 hours and then solid sodium sulfite was added until starch paper indicated that no more peroxides were present. The reaction mixture was extracted with ethyl acetate (4×1 vol). The ethyl acetate layer was dried over magnesium sulfate filtered and concentrated. The crude material was dissolved in dichloromethane (300 ml) and the solution was cooled to 0° C. then celite (25 g) and PCC (57 g) were added in five portions over 20 minutes. The reaction mixture was warmed to room temperature and stirred overnight. The solution was then diluted with ether and filtered through a pad of a mixture of celite and florisil. Purification by flash chromotgraphy (silica gel, hexane/ethyl acetate, 5:1 to 3:1) gave 58.6 g of the title compound. $^1$H NMR (200 MHz, CDCl$_3$): 7.75–7.60 (m, 2H), 7.50–7.44 (m, 2H), 4.30–4.15 (m, 2H), 2.85 (dt, 2H), 2.63 (s, 2H), 1.98 (dt, 2H), 1.53–1.40 (m, 2H), 1.49 (s, 9H).

Step B: Preparation of 3-[(trifluoromethanesulfonyl)oxy]-1'-(t-butyloxycarbonyl)spiro[1H-indene-1,4'-piperidine]

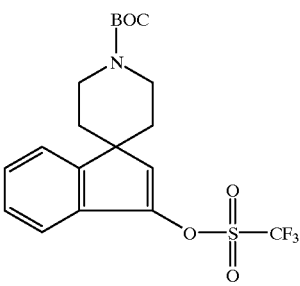

Potasium bis(trimethylsilyl)amide (127.5 ml, 0.5M) was added to the ketone of Step A (16.0 g, 53 mmol) in THF (200 mL) at 0° C. The reaction mixture was stirred for one hour and then N-phenyltrifluromethanesulfonamide was added. The ice bath was allowed to melt and the reaction mixture was stirred overnight at room temperature. Water was added and the aqueous layer was extracted with ethyl acetate (3×1 vol). The organic layer was washed with brine and then dried over magnesium sulfate, filtered and then concentrated. The crude product was purified by flash chromatography (hexane/ethyl acetate 8:1) to give the title compound (17.8 g) as a waxy solid. $^1$HNMR (200 MHz, CDCl$_3$): 7.65–7.14 (m, 4 H), 6.66 (s, 1 H), 4.30–4.15 (m, 2 H), 3.24–2.96 (m, 2H), 2.06 (dt, 2 H), 1.50 (s, 9 H), 1.49–1.38 (m, 2 H).

Step C: Preparation of 3-(ethoxycarbonyl)-1'-(t-butyloxycarbonyl)spiro[1H-indene-1,4'-piperidine]

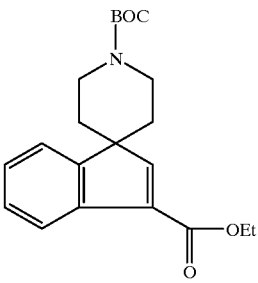

A solution of 17.4 g of the intermediate from Step B, 11.0 ml of triethylamine, 634 mg of triphenylphosphine, and 240 mg of palladium acetate in 72 ml of ethanol and 158.0 ml of DMF was purged for 10 minutes with carbon monoxide and then stirred under a carbon monoxide atmosphere for 24 hours. The ethanol was removed in vacuum and the reaction mixture was diluted with water and extracted repeatedly with ethyl acetate. The ethyl acetate layer was washed with 1N HCl, water, and brine and then dried over magnesium sulfate, filtered and concentrated. Purification by flash chromatography (hexane/ethyl acetate 8:1) provided 27.6 g of the title compound as a colorless oil. ¹HNMR (200 MHz, CDCl₃): 8.0–7.94 (m, 1H), 7.7 (s, 1 H), 7.4–7.25 (m, 3H), 4.4 (q, 2H), 4.25–4.15 (m, 2H), 3.13 (dt, 2H), 2.03 (dt, 2H), 1.5 (s, 9H), 1.55–1.35 (m, 2H), 1.4 (t, 3H).

Step D: Preparation of 3-(carboxy)-1'-(t-butyloxycarbonyl)spiro[1H-indan-1,4'-piperidine]

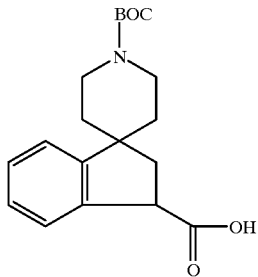

To a suspension of Pd/C (1.7 g) in ethanol (300 ml) was added the title compound (27 g) from Step C. The reaction mixture was purged with hydrogen and then shaken under a hydrogen atmosphere for 3 hours. The mixture was purged with nitrogen and filtered through celite and concentrated to give the title compound (27 g). The crude product was dissolved in ethanol (200 ml) and 2N sodium hydroxide (76 ml) was added. The reaction mixture was heated to 50° C. for three hours then cooled and the ethanol was removed under vacuum and the residue was dissloved in ethyl acetate. 1N HCl was added and the layers were separated and the aqueous layer was extracted with ethyl acetate (3×1 vol). The combined organic layers were washed with saturated aqueous NaCl, dried over anhydrous sodium sulfate, filtered and concentrated to provide the title compound (23.8 g) as a white solid. ¹HNMR (200 MHz, CDCl₃): 7.50–7.42 (m, 1 H), 7.34–7.12 (m, 3 H), 4.22–4.04 (m, 3 H), 3.06–2.84 (m, 2 H), 2.40 (d, 2 H), 1.88–1.6 (m, 4 H), 1.50 (s, 9 H).

Step E: Preparation of 3S-3-(carboxy)-1'-(t-butyloxycarbonyl)spiro[1H-indan-1,4'-piperidine]

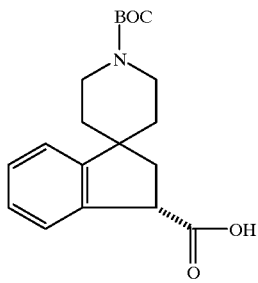

The acid from Step D (23.5 g, 0.07 mol) was dissolved in toluene (150 ml) and R-methylbenzylamine (9.02 ml) was added. The toluene solution was heated on a steam bath until everything was in solution. The solution was then seeded with crystals grown in the same way on a much smaller scale. The solution was allowed to sit overnight and then the mixture was filtered to give 15.8 g of crystals. The crystals were recrystalized from toluene two more times. The crystals (12 g) were dissolved in ethyl acetate/1N HCl and the organic layer was washed with 1N HCL (2×1 vol) and brine. The organic layer was dried over magnesium sulfate, filtered and concentrated to give 8.9 g of the title compound. $[\alpha]^D = -16.9$ (c=0.84, methanol)

Step F: Preparation of 3R-3-(carboxy)-1'-(t-butyloxycarbonyl)spiro[1H-indan-1,4'-piperidine]

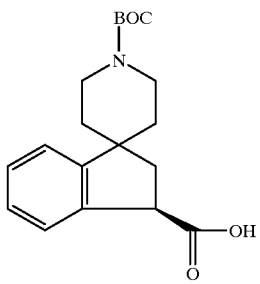

The mother liqueurs from Step E were washed with 1N HCl (2×1 vol) and brine dried over magnesium sulfate, filtered, and concentrated to give recovered acid (15.4 g). To this acid in toluene (100 mL) was added S-methylbenzylamine (5.95 mL). The crystals were recrystallized four times from toluene as above to give 12.3 g of salt. The salt was dissolved in ethyl acetate/1N HCl and washed with 1N HCl (2×1 vol) and brine. The organic layer was dried over magnesium sulfate and filtered and concentrated to give the title compound (9.0 g). $[\alpha]^D = +17.1$ (c=1.06, methanol).

Step G: Preparation of 3R-3-[[(benzyloxy)carbonyl]amino]-1'-(t-butyloxycarbonyl)spiro[1H-indan-1,4'-piperidine]

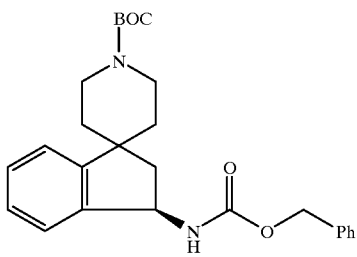

To a stirred solution of 3R-3-(carboxy)-1'-(t-butyloxycarbonyl)spiro[1H-indan-1,4'-piperidine] (3.56 gm, 10.76 mmol) in dry toluene (30 mL) was added triethylamine (1.52 gm, 15.06 mmol), DPPA (3.55 gm, 12.91 mmol) and the mixture heated to 85° C. for four hours to form 3R-3-(isocyanato)-1'-(t-butyloxycarbonyl)spiro[1H-indan-1,4'-piperidine]. The mixture was cooled to r.t. and benzyl alcohol (1.40 gm, 12.91 mmol) added and the reaction mixture stirred an additional 1.5 hr. The mixture was diluted with 50 ml of ethyl acetate and washed with 1N HCl, brine and dried over MgSO₄. Concentrate and chromatograph (SiO₂, 1:1 EtOAc/hexane) to provide 4.1 grams of the clear, colorless viscous oil that is the title compound. ¹HNMR: (CDCl₃; 300 Mhz). ESI-MS calc. for C26H32N2O4: 436; Found 454 (M+H+NH₃).

Step H: Preparation of 3R-3-amino-1'-(t-butyloxycarbonyl) spiro[1H-indan-1,4'-piperidine] hydrochloride salt

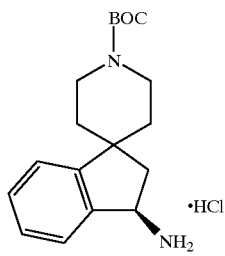

To a stirred solution of the product of Step G (4.1 gm, 9.4 mmol) in methanol (50 mL) was added HCl$_{(conc.)}$ (0.9 mL, 10.3 mmol) and Pd(OH)$_2$—C (0.5 gm). The mixture was stirred vigorously under an H$_2$ atomosphere for 16 hr. The reaction mixture was filtered through celite and the solvent removed in vacuo to provide 2.85 gm of the white solid. ESI-MS calc. for C18H26N2O2: 302; Found 303 (M+H), 203 (M+H-Boc).

INTERMEDIATE 11

3R-3-(acetylamino)-spiro[1H-indan-1,4'-piperidine] HCl

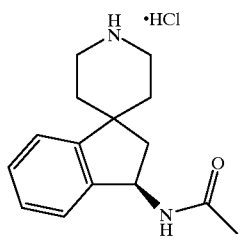

To a stirred solution of Intermediate 10 (1.5 gm, 4.4 mmol) and DMAP (54 mg, 0.4 mmol) in dry dichloromethane (15 mL) was added triethylamine (1.3 gm, 13.3 mmol), acetic anhydride (0.68 gm, 6.6 mmol) and the mixture stirred for 16 hr. The reaction mixture was concentrated, diluted with 50 ml of ethyl acetate and washed with NaHCO$_3$ (sat'd), brine and dried over MgSO$_4$. The organic phase was concentrated and chromatographed (SiO$_2$, 3:1:0.1 EtOAc/hexane/methanol) to provide 1.6 grams (81%) of the N-Boc protected title compound as white solid. ESI-MS calc. for C20H28N2O3: 344; Found 345 (M+H).

To a stirred solution of N-Boc protected title compound (1.2 g, 3.6 mmol) in methanol (1.0 mL), HCl-EtOAc was added to the mixture (5 mL). The reaction was stirred for 20 minutes and the solvent was removed in vacuo to afford 0.95 g of the product. ESI-MS calc. for C15H20N2O: 244; Found 245 (M+H), 286 (M+H+CH3CN).

INTERMEDIATE 12

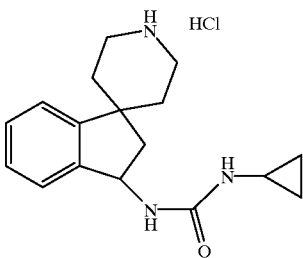

The general procedure described in Step G of Intermediate 10 was followed using cyclopropylamine instead of benzyl alchol to react with the isocyanato compound to provide the N-Boc protected title compound. The N-Boc protecting group was removed according to the general procedure described in Intermediate 11 to provide the title compound.

INTERMEDIATES 13–24

Following the general procedure described for Intermediate 11, and using Intermediate 10 and the appropriate acylating agent, or following the general procedure described for Intermediate 12 using the appropriate amine to react with the isocyanato compound described in Intermediate 10, step G, Intermediates 13–24 were prepared.

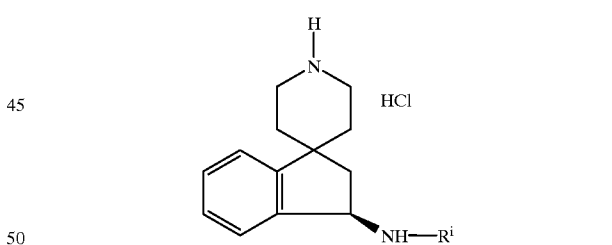

| Intermediate | Acylating Agent/Amine | $R^i$ |
|---|---|---|
| 13 | methanesulfonyl chloride | SO$_2$CH$_3$ |
| 14 | 3-pyridinecarbonyl chloride | CO-3 pyridyl |
| 15 | 4-pyridinecarbonyl chloride | CO-4-pyridyl |
| 16 | 2-pyrazinecarbonyl chloride | CO-2-pyrazinyl |
| 17 | 2-aminopyrimidine | CONH-2-pyrimidinyl |
| 18 | piperidine | CO—N(CH$_2$)$_5$ |
| 19 | morpholine | CO—N(CH$_2$)$_2$O(CH$_2$)$_2$ |
| 20 | 2-aminothiazole | CONH-2-thiazolyl |
| 21 | 2-pyridinecarbonyl chloride | CO-2-pyridyl |
| 22 | benzoyl chloride | CO—Ph |
| 23 | benzenesulfonyl chloride | SO$_2$Ph |
| 24 | 2-thiophenecarboxylic acid | CO-2-thienyl |

INTERMEDIATE 25

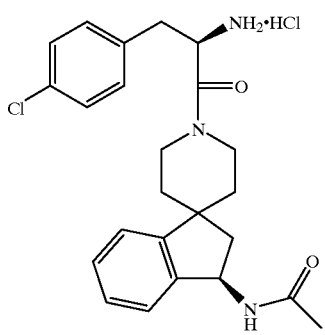

To a stirred solution of Intermediate 11 (657 mg, 2.34 mmol), N-Boc-D-4-chlorophenylalanine (737 mg, 2.5 mmol), PyBrop (1091 mg, 2.34 mmol) and DMAP (172 mg, 1.4 mmol) in dichloromethane, 6 mL was added DIEA (907 mg, 7.02 mmol). The solution was stirred 16 hr, concentrated and chromatographed directly (SiO$_2$,19:1 EtOAc/methanol) to provide 1.08 gm of the N-Boc protected title compouns as a white solid. ESI-MS calc. for C29H36ClN3O4: 525; Found 526 (M+H), 426 (M+H-Boc).

To a stirred solution of the N-Boc protected title compound from the previous step (1.1 g, 2.1 nunol) in methanol (0.5 mL), HCl-EtOAc was added (5 mL). The reaction was stirred for 20 minutes and the solvent was removed in vacuo to afford 0.95 g of the title compound. ESI-MS calc. for C24H28ClN3O2: 425; Found 426 (M+H), 443 (M+H+NH$_3$).

INTERMEDIATE 26–38

Following the procedure described for Intermediate 25 and unsing Intermediates 12–24, the following compounds were prepared:

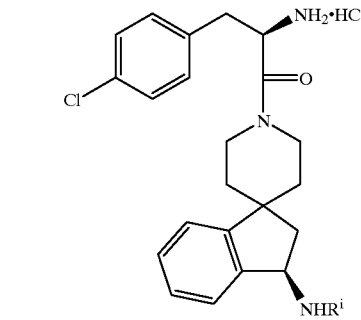

| Intermediate | R$^i$ |
|---|---|
| 26 | CONH-cyclopropyl |
| 27 | SO$_2$CH$_3$ |
| 28 | CO-3-pyridyl |
| 29 | CO-4-pyridyl |
| 30 | CO-2-pyrazinyl |
| 31 | CONH-2-pyrimidinyl |
| 32 | CO—N(CH$_2$)$_5$ |
| 33 | CO—N(CH$_2$)$_2$O(CH$_2$)$_2$ |
| 34 | CONH-2-thiazolyl |
| 35 | CO-2-pyridyl |
| 36 | CO—Ph |

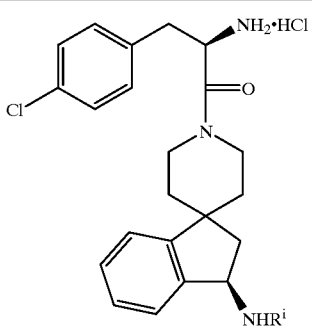

| Intermediate | R$^i$ |
|---|---|
| 37 | SO$_2$Ph |
| 38 | CO-2-thienyl |

A heterogeneous mixture of the product of Intermediate 10, Step F (5.0 gm, 15.1 mmol), Rh/Al$_2$O$_3$ (0.85 gm) in ethanol (50 mL) was agitated under an atmosphere of hydrogen (2000 psi, 100° C.) for 18 hr. The mixture was filtered through celite and the solvent removed in vacuo to provide (3.85 gm) (75%) of the white solid which is the title compound. ESI-MS calc. for:; Found (M+H).

INTERMEDIATE 40

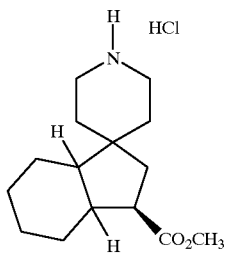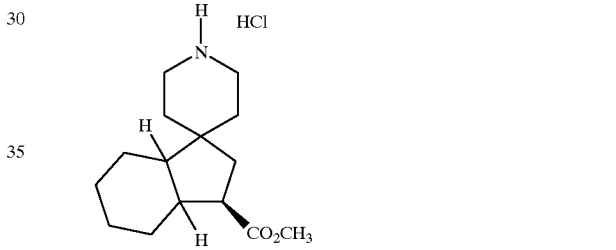

To a stirred solution of HCl-MeOH (mL) was added Intermediate 39 (350 mg, 104 mmol) and the mixture stirred 16 hr. The solvent was removed in vacuo to provide (300 mg) (100%) of the white solid which is the title compound. ESI-MS calc. For C15H26ClNO2: 287; Found 288(M+H).

INTERMEDIATE 41

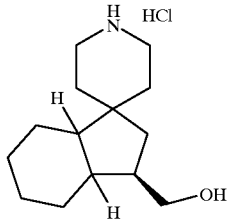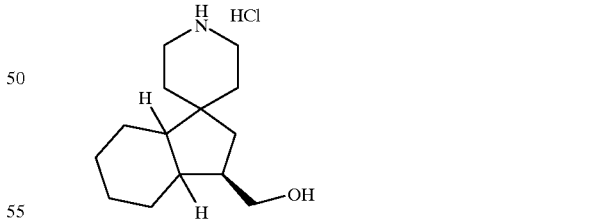

Step A.

In a dry three-necked round-bottomed flask equipped with magnetic stir bar and nitrogen purge, was added Intermediate 39 (2.5 gm, 7.41 mmol) and tetrahydrofuran (7.5 mL, anhydrous). The mixture was stirred and cooled to −10° C. and borane-dimethylsulfide (7.4 mL, 2M in THF, 2 eq.) was added dropwise over a period of 20 min. When the addition was complete, the mixture was warmed to r.t., refluxed for one hour, and cooled to r.t. The reaction was quenched with the addition of 1 mL water/acetic acid accompanied by vigorous stirring. The mixture was concentrated under reduced pressure, diluted with ethyl acetate, washed with saturated NaHCO3, brine and then dried over MgSO4. The solvent was removed in vacuo to provide (2.32 gm) (97%) of the white solid which is the N-Boc protected title compound. ESI-MS calc. For C19H33NO3: 323; Found 324(M+H).

Step B.

To a stirred mixture of N-Boc protected title compound (180 mg, 0.4 mmol.) in a minimal amount of methanol (ca. 100 μL) was added 5 mL of a saturated HCl-EtOAc solution. The mixture was stirred 20 min and the solvent removed in vacuo to provide (154 mg) of the white solid which is the title compound. ESI-MS calc. For C14H26ClNO: 260; Found 261(M+H).

INTERMEDIATE 42

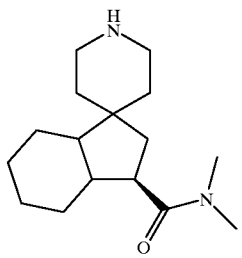

To a stirred solution of Intermediate 39 (400 mg, 1.2 mmol), PyBrop (607 mg, 1.2 mmol) and DMAP (92 mg, 0.7 mmol) in dichloromethane, 2.0 mL was added DIEA (459 mg, 3.6 mmol). The reaction mixture was stirred 16 hr, diluted with dichloromethane, washed with 1N HCl and concentrated in vacuo. The residue was purified via preparative HPLC to provide 435 mg of the white solid that is the N-Boc protected title compound. ESI-MS calc. For C21H36N2O3: 364; Found 365(M+H).

The procedure described in Step B of Intermediate 41 was followed using the N-Boc protected title compound to provide the title compound. ESI-MS 265 (M+H).

INTERMEDIATE 43

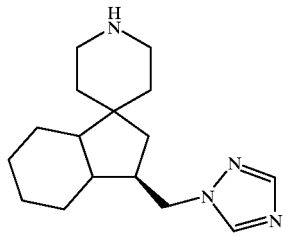

To a solution of intermediate 41 (1.8 gm, 5.6 mmol) in dichloromethane (15 mL) add triethylamine (1.69 gm, 3.0 eq) stir and cool to 0° C., then add mesyl chloride (1.0 gm, 1.5 eq) and continue stirring three hours. Concentrate, dilute with DMF (6 mL), stir and add sodium triazole (1.0 gm, 3 eq.). dilute with ethyl acetate then wash with saturated NaHCO3, brine and dry over MgSO4. Remove solvent in vacuo to provide (154 mg) of the yellow solid which is the N-Boc protected title compound. ESI-MS calc. For C21H32N4O3: 388; Found 389(M+H).

The procedure described in Step B of Intermediate 41 was followed using the N-Boc protected title compound to provide the title compound. ESI-MS 289 (M+H).

INTERMEDIATE 44

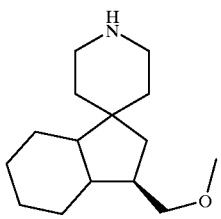

To a solution of intermediate 41 (0.5 gm, 1.5 mmol) in tetrahydrofuran (5 mL) was added imidazole (105 mg, 1.0 eq), and the mixture was stirred and cooled to 0° C., then sodium hydride (74 mg, 2.0 eq) was added thereto and stirring continued for 30 min. Methyl iodide (439 mg, 2 eq.) was added via syringe, and the mixture was warmed to r.t. and stirring was contined for 2 hr. The reaction mixture was concentrated and partitioned between EtOAc/1N HCl, washed with brine and dried over MgSO$_4$. The solvent was removed in vacuo to provide (250 mg) of the yellow oil which is the title N-protected title compound. ESI-MS calc. For C20H35NO3: 337; Found 338(M+H).

The procedure described in Step B of Intermediate 41 was followed using the N-Boc protected title compound to provide the title compound. ESI-MS 238 (M+H).

The following Examples are provided to illustrate the invention, and are not to be construed as limiting the scope of the invention in any manner.

EXAMPLE 1

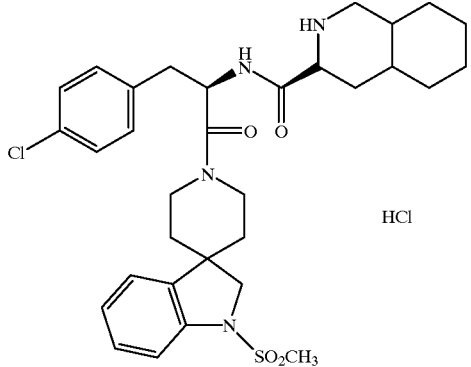

Step A: Preparation of 3S-N-Boc-3-decahydroisoquinolinecarboxylic acid

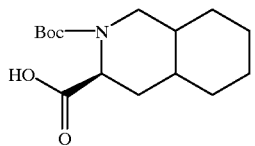

A 50-mL, three-necked, round-bottomed flask equipped with an nitrogen inlet adapter, glass stopper, and rubber septum was charged with commercially available N-Boc-(L)-Tic (1.00 g, 3.6 mmol) and 18 mL of DMF. Potassium carbonate (0.597 g, 4.30 mmol) was then added followed by the addition of methyl iodide (1.1 mL, 18.0 mmol) via syringe. The resulting mixture was stirred at room temperature for 20 h and then methylene chloride and water were added. The aqueous layer was separated and extracted with two portions of methylene chloride, and the combined organic phases were washed with saturated sodium chloride solution, dried over sodium sulfate, filtered, and concentrated. The crude product was purified by flash chromatography (1:1 ethyl acetate-hexane) to give N-Boc-(L)-Tic methyl ester (1.17 g) as a yellow oil.

A solution of N-Boc-(L)-Tic methyl ester (1.05 g, 3.60 mmol) and 12 mL of methanol was charged with 5% rhodium on alumina (0.53 g) and then heated at 55–60° C. under 40 psi of hydrogen for 36 h. After cooling to room temperature, the reaction mixture was filtered through Celite using methanol to rinse and concentrated. The crude oil was then filtered again through Celite using ethyl acetate as the eluent and concentrated to give methyl 3S-N-Boc-3-decahydroisoquinoline-carboxylate (0.733 g) as a clear oil. ESI-MS calcd for $C_{16}H_{27}NO_4$: 297: Found: 298 (m+1). Hydrogenation of a similar compound gave exclusively the cis-ring junction products as a mixture of diastereomers, see: Ornstein, P. L.; Arnold, M. B.; Augenstein, N. K.; Paschal, J. W. *J. Org. Chem.* 1991, 56, 4388.

A 25-mL, round-bottomed flask was charged with methyl 3S-N-Boc-3-decahydro-isoquinolinecarboxylate (0.733 g, 2.46 mmol) and 7 mL of methanol. An aqueous 1N NaOH solution (5 mL) was then added and the resulting mixture was stirred at room temperature for 22 h. The mixture was then concentrated and the resulting residue was dissolved in water and cooled at 0° C. in an ice-water bath. The pH was then adjusted using a 1N HCl to pH 4, and the cloudy mixture was diluted with ethyl acetate. The aqueous layer was separated and extracted with two portions of ethyl acetate, and the combined organic phases were washed with saturated sodium chloride solution, dried over sodium sulfate, filtered, and concentrated to give 3S-N-Boc-3-decahydro-isoquinoline-carboxylic acid (0.667 g) as a very thick yellow oil. The $^1$H NMR spectrum shows the presence of two diastereomers; cis-ring junction isomers from the previous hydrogenation reaction.

Step B: Preparation of Title Compound

A 25-mL, round-bottomed flask was charged with Intermediate 1 (0.102 g, 0.182 mmol) and then a solution of the acid of Step A (0.057 g, 0.201 mmol) in 1.2 mL of methylene chloride was added. The mixture was cooled at 0° C. in an ice-water bath and then NMM (0.10 mL, 0.910 mmol), HOBt.H$_2$O (0.027 g, 0.201 mmol), and EDC.HCl (0.039 g, 0.201 mmol) were added. The resulting mixture was stirred at room temperature for 22 h, and was then diluted with methylene chloride and washed with two portions of 1N HCl solution, saturated sodium bicarbonate solution, water, and saturated sodium chloride solution, dried over sodium sulfate, filtered, and concentrated. The crude product was purified by flash chromatography (9:1 methylene chloride:acetone) to give the N-Boc protected title compound (0.096 g) as a white solid. ESI-MS calcd for $C_{37}H_{49}N_4SO_6Cl$: 712: Found: 713 (m+1). The $^1$H NMR spectrum shows the presence of two cis-ring junction diastereomers from the hydrogenation reaction.

A 25-mL, round-bottomed flask was charged with the N-Boc protected title compound (0.080 g, 0.112 mmol) and 0.3 mL of methylene chloride. Trifluoroacetic acid (0.3 mL) was then added and the mixture was stirred at room temperature for 65 min. The mixture was diluted with toluene and concentrated, and the resulting oil was diluted with toluene again and concentrated. The residue was dissolved in ethyl acetate and washed with 1N NaOH solution, and the combined organic phases were dried over potassium carbonate, filtered, and concentrated to give a clear oil. The free amine was then dissolved in 0.5 mL of ethyl acetate and 0.13 mL of a 1N HCl solution in ether was added dropwise via syringe. The mixture was diluted with ether and the precipitate was then filtered under nitrogen to give the title compound (0.056 g) as a white powder. ESI-MS calcd for $C_{32}H_{41}N_4SO_4Cl$: 612: Found: 613 (m+1).

EXAMPLE 2

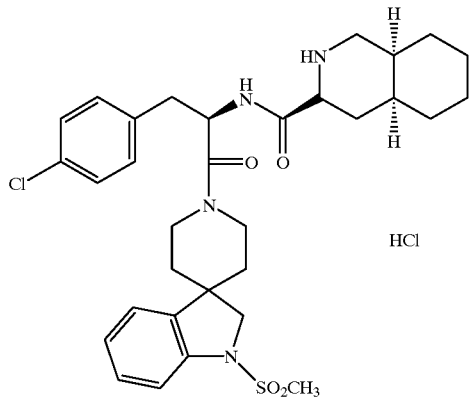

Step A: Preparation of [3S(3α,4aβ,8aβ)]-N-Boc-decahydro-3-isoquinolinecarboxylic acid

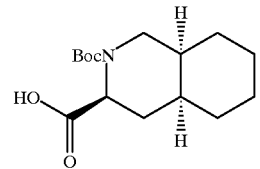

A 25-mL, round-bottomed flask equipped with a reflux condenser was charged with commercially available [3S(3α,4aβ,8aβ)]-N-tert-butyldecahydro-3-isoquinolinecarboxamide (1.0 g, 4.19 mmol) and 10 mL of aqueous 6N HCl solution. The solution was heated at 80° C. for 23 h and then cooled to 0° C. and diluted with 12 mL of 5N NaOH solution (pH=13). The aqueous solution was extracted with ethyl acetate and then transferred to a 100-mL, round-bottomed flask and diluted with 25 mL of dioxane. Di-tert-butyl dicarbonate (1.0 g, 4.61 mmol) was then added and the mixture was stirred at room temperature for 23.5 h while occasionally adjusting the pH using 5N NaOH solution (pH=10). The resulting mixture was diluted with ethyl acetate and water and the layers were separated. The aqueous layer was cooled at 0° C. in an ice-water bath and then 1N HCl solution was added portionwise until pH=2. The aqueous layer was extracted with three portions of ethyl acetate, and the combined organic phases were washed with saturated sodium chloride solution, dried over sodium sulfate, filtered, and concentrated to give [3S(3α,4aβ,8aβ)]-N-Boc-decahydro-3-isoquinolinecarboxylic acid (0.427 g) as a white solid.

Step B: Preparation of Title Compound

A 25-mL, round-bottomed flask was charged with Intermediate 1 TFA salt (prepared as Intermediate 1 except TFA is used in place of HCl, 0.123 g, 0.219 mmol) and 1.3 mL of methylene chloride and then the mixture was cooled at 0° C. in an ice-water bath. Acid from Step A (0.068 g, 0.241 mmol), NMM (0.10 mL, 0.910 mmol), HOBt.H$_2$O (0.033 g, 0.241 mmol), and EDC.HCl (0.046 g, 0.241 mmol) were added. The resulting mixture was stirred at room temperature for 22 h, and was then diluted with methylene chloride and washed with two portions of 1N HCl solution, saturated sodium bicarbonate solution, water, and saturated sodium chloride solution, dried over sodium sulfate, filtered, and concentrated. The crude product was purified by flash chromatography (9:1 methylene chloride:acetone) to give N-Boc protected title compound (0.112 g) as a white solid. ESI-MS calcd for $C_{37}H_{49}N_4SO_6Cl$: 712: Found: 713 (m+1).

A 25-mL, round-bottomed flask was charged with the N-Boc protected title compound (0.110 g, 0.154 mmol) and 0.4 mL of methylene chloride. Trifluoroacetic acid (0.4 mL) was then added and the mixture was stirred at room temperature for 45 min. The mixture was diluted with toluene and concentrated, and the resulting oil was diluted with toluene again and concentrated. The residue was dissolved in ethyl acetate and washed with 1N NaOH solution (back-extracted with two portions of ethyl acetate), and the combined organic phases were dried over potassium carbonate, filtered, and concentrated to give a yellow oil. The free amine was then dissolved in 0.5 mL of ethyl acetate and 0.18 mL of a 1N HCl solution in ether was added dropwise via syringe. The mixture was diluted with ether and the precipitate was then filtered under nitrogen to give the title compound (0.072 g) as a white powder. ESI-MS calcd for $C_{32}H_{41}N_4SO_4Cl$: 612: Found: 613 (m+1).

EXAMPLE 3

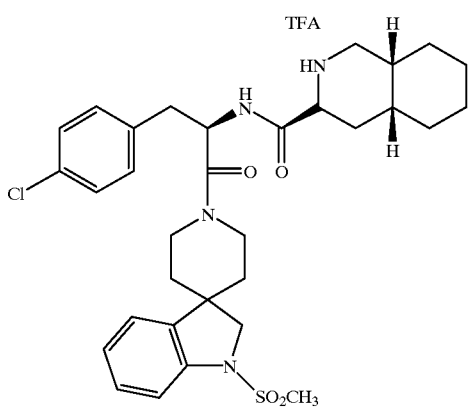

Step A: Preparation of [3S(3α,4aα,8aα)]-N-Boc-decahydro-3-isoquinolinecarboxylic acid, (R)-α-methylbenzylamine salt

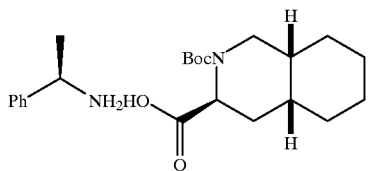

A 25-mL, round-bottomed flask was charged with acid 3S-N-Boc-3-decahydroisoquinolinecarboxylic acid from Example 1 (0.453 g, 1.60 mmol) and 14 mL of ethyl acetate. (R)-α-methylbenzyl amine (0.21 mL, 1.60 mmol) was then added and the resulting mixture sat at room temperature under nitrogen for 24 h. The precipitate was then filtered to give 0.393 g of a white powder. The white powder was then recrystallized (ethyl acetate-ethanol) to give [3S(3α,4aα,8aα)]-N-Boc-decahydro-3-isoquinolinecarboxylic acid, (R)-α-methylbenzylamine salt (0.130 g) as a white solid.

Step B: Preparation of Title Compound

A 15-mL, round-bottomed flask was charged with the free acid of the product of Step A (obtained by washing intermediate from Step A with 10% aqueous citric acid) (0.020 g 0.049 mmol) and 0.3 mL of methylene chloride. Intermediate 1 (0.022 g, 0.045 mmol), NMM (0.020 mL, 0.180 mmol), HOBt.H$_2$O (0.007 g, 0.049 mmol), and EDC.HCl (0.009 g, 0.047 mmol) were added. The resulting mixture was stirred at room temperature for 17 h, and was then diluted with methylene chloride and washed with two portions of 1N HCl solution, saturated sodium bicarbonate solution, water, and saturated sodium chloride solution, dried over sodium sulfate, filtered, and concentrated. The crude product was purified by flash chromatography (1:1 ethyl acetate-hexane) to give N-Boc protected title compound (0.023 g) as a white solid.

A 10-mL, round-bottomed flask was charged with the N-Boc protected title compound (0.022 g, 0.031 mmol) and 0.2 mL of methylene chloride. Trifluoroacetic acid (0.2 mL) was then added and the mixture was stirred at room temperature for 1 h. The mixture was diluted with toluene and concentrated twice, and then the oil was diluted with ether and concentrated to afford the title compound (0.021 g) as a white solid. ESI-MS calcd for $C_{32}H_{41}N_4SO_4Cl$: 612: Found: 613 (m+1).

EXAMPLE 4

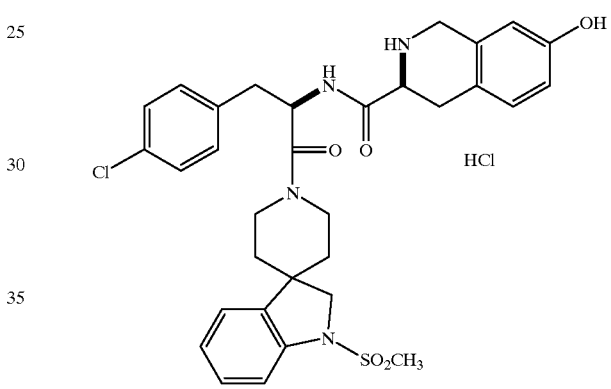

To a solution of Intermediate 1 (450.1 mg, 1.01 mmol) in methylene chloride (10 mL) was added N-Boc-7-hydroxy-L-1,2,3,4-tetrahydroquinoline-3-carboxylic acid (7-OH-N-Boc-L-Tic, 355.5 mg, 1.21 mmol), HOBt (164.1 mg, 1.21 mmol), EDC (232.3 mg, 1.21 mmol), and NMM (0.5 mL, 4.55 mmol). The mixture was stirred at room temperature overnight and then quenched with EtOAc (50 mL). The organic solution was washed with 5% aq HCl solution (50 mL), saturated aqueous NaHCO$_3$ (50 mL), and brine (50 mL), and dried over anhydrous Na$_2$SO$_4$, filtered, and concentrated. The crude product was purified by MPLC (4:1 DCM:aceton) to give the N-Boc protected title compound as a white solid (558.8 mg, 76.6%). ESI-MS calc. for $C_{37}H_{43}ClN_4O_7S$ 722; Found 723 (M+1).

To a solution of N-Boc protected title compound (79.5 mg, 109.9 μmol) and anisole (0.1 mL) in DCM (1.0 mL) was added TFA (0.5 mL). The mixture was stirred at room temperature until no starting material left (TLC). The solvents were removed under reduced pressure and diethyl ether was added to give a white solid (TFA salt). The salt was added to an aquoues solution of 1N NaOH (15 mL) and extracted with ethyl acetate (2×15 mL). The combined organics were dried over anhydrous Na$_2$SO$_4$, filtered, and concentrated. The residue was dissolved in ethyl acetate (0.5 mL) to which was added 1N HCl in diethyl ether to yield the title compound as a white solid (53.6 mg, 73.9%, HCl salt). ESI-MS calc. for $C_{32}H_{35}ClN_4O_5S$ 622; Found 623 (M+1).

EXAMPLE 5

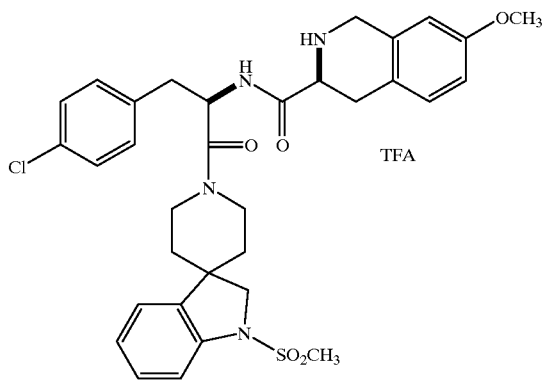

To a mixture of the N-Boc protected compound of Example 4 (153.4 mg, 212.1 μmol) and $K_2CO_3$ (58.8 mg, 425.5 μmol) in DMF (5.0 mL) was added methyl iodide (20.0 μL, 321.4 μmol). The mixture was stirred at room temperature overnight and then quenched with 1N HCl (aquoues, 50 mL), and extracted with ethyl acetate (3×50 mL). The combined organic layers were washed with saturated aqueous $NaHCO_3$ (50 mL) and brine (50 mL), dried over anhydrous $Na_2SO_4$, filtered, and concentrated to afford the N-Boc protected title compound as a colorless oil (147.0 mg, 94.0%). ESI-MS calc. for $C_{38}H_{45}ClN_4O_7S$ 736; Found 737 (M+1).

To a solution of the N-Boc protected title compound (179.9 mg, 244.0 μmol) and anisole (0.1 mL) in DCM (2.0 mL) was added TFA (1.0 mL). The mixture was stirred at room temperature until no starting material left (TLC). The solvents were removed under reduced pressure and diethyl ether was added to provids the title compound as a white solid (143.2 mg, 78.1%). ESI-MS calc. for $C_{33}H_{37}ClN_4O_5S$ 636; Found 637 (M+1).

EXAMPLES 6–15

The general procedure described in Example 4 was followed to provide compounds of Examples 6–15 using the Intermediates and acids listed below:

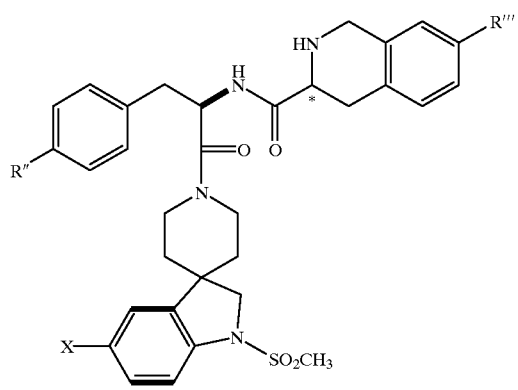

Stereoconfiguration same as the Tic starting material

| Ex. | Interm. | Acid | Salt | $R^{ii}$ | $R^{iii}$ | x | EI-MS |
|---|---|---|---|---|---|---|---|
| 6 | 3 | N-Boc-D-Tic | TFA | Br | H | H | 651 (M + 1) |
|   |   |   |   |   |   |   | 653 (M + 3) |
| 7 | 3 | N-Boc-L-Tic | TFA | Br | H | H | 651 (M + 1) |
|   |   |   |   |   |   |   | 653 (M + 3) |
| 8 | 4 | 7-OH—N-Boc-L-Tic | TFA | Cl | OH | F | 641 (M + 1) |
| 9 | 3 | 7-OH—N-Boc-D-Tic | TFA | Br | OH | H | 667 (M + 1) |
|   |   |   |   |   |   |   | 669 (M + 3) |
| 10 | 3 | 7-OH—N-Boc-L-Tic | TFA | Br | OH | H | 667 (M + 1) |
|   |   |   |   |   |   |   | 669 (M + 3) |
| 11 | 1 | 7-OH—N-Boc-D-Tic | TFA | Cl | OH | H | 623 (M + 1) |
| 12 | 5 | N-Boc-L-Tic | TFA | $CH_3$ | H | H | 587 (M + 1) |
| 13 | 1 | N-Boc-D-Tic | HCl | Cl | H | H | 653 (M + H) |
| 14 | 2 | N-Boc-D-Tic | HCl | $CH_3O$ | H | H |  |
| 15 | 2 | N-Boc-L-Tic | HCl | $CH_3O$ | H | H |  |

EXAMPLE 16

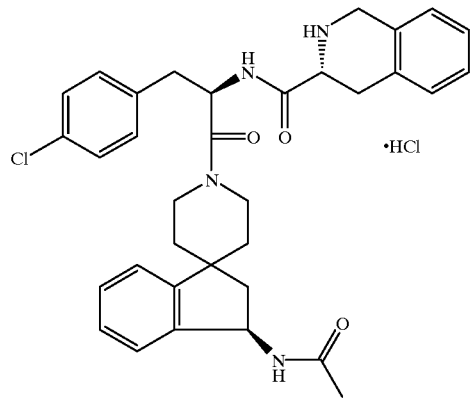

To a stirred solution of Intermediate 25 (150 mg, 0.35 mmol), N-Boc-D-Tic (162 mg, 0.35 mmol), PyBrop (164 mg, 0.35 mmol) and DMAP (172 mg, 1.4 mmol) in dichloromethane, 6 mL was added DIEA (26 mg, 0.21 mmol). The solution was stirred 16 hr, concentrated and chromatographed directly ($SiO_2$,19:1 EtOAc/methanol) to provide 200 mg of the N-Boc protected title compound as a white solid. ESI-MS calc. for C39H45ClN4O5: 684; Found 685 (M+H), 585 (M+H-Boc).

To a stirred solution of the N-Boc protected title compound from the previous step (160 mg, 0.23 mmol) in methanol (0.25 mL), HCl-EtOAc was added (5 mL). The reaction was stirred for 20 minutes and the solvent was removed in vacuo to afford 138mg of the title compound as a white solid. ESI-MS calc. for C34 H37N4 O3 Cl1: 584; Found 585 (M+H), 607 (M+H+$NH_3$).

EXAMPLES 17–29

The general procedure described in Example 13 was followed using Intermedates 26–38 to synthesize the following compounds:

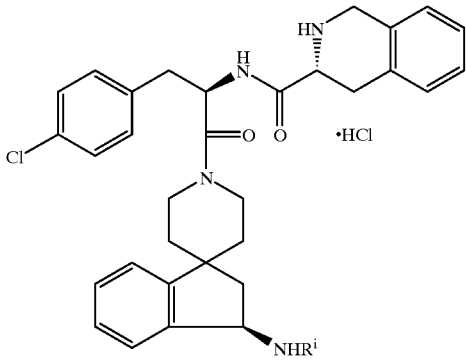

| Example | Intermediate | $R^i$ | EI-MS |
|---|---|---|---|
| 17 | 26 | CONH-cyclopropyl | |
| 18 | 27 | $SO_2CH_3$ | |
| 19 | 28 | CO-3-pyridyl | |
| 20 | 29 | CO-4-pyridyl | |
| 21 | 30 | CO-2-pyrazinyl | 649 (M + H) |
| 22 | 31 | CONH-2-pyrimidinyl | 664 (M + H) |
| 23 | 32 | CO—$N(CH_2)_5$ | 654 (M + H) |
| 24 | 33 | CO—$N(CH_2)_2O(CH_2)_2$ | 656 (M + H) |
| 25 | 34 | CONH-2-thiazolyl | 669 (M + H) |
| 26 | 35 | CO-2-pyridyl | 648 (M + H) |
| 27 | 36 | CO—Ph | 647 (M + H) |
| 28 | 37 | $SO_2Ph$ | 683 (M + H) |
| 29 | 38 | CO-2-thienyl | 653 (M + H) |

EXAMPLE 30–34

Following the general procedures described for Intermediate 25 and Example 16 and starting with Intermediates 40–44, the following compounds were prepared:

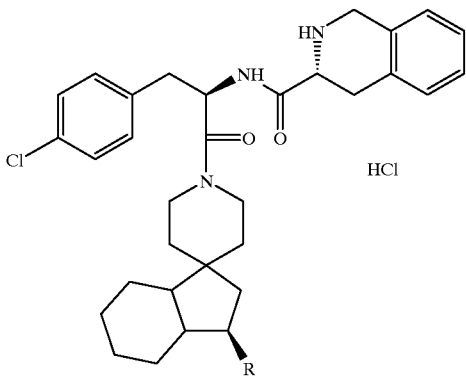

| Example | Intermediate | $R^i$ | ESI-MS |
|---|---|---|---|
| 30 | 40 | $CO_2CH_3$ | 592 (M + H) |
| 31 | 42 | $C(O)N(CH_3)_2$ | 603 (M + H) |
| 32 | 43 | $CH_2$-1,2,4-triazol-1-yl | 615 (M + H) |
| 33 | 41 | $CH_2OH$ | 564 (M + H) |
| 34 | 44 | $CH_2OCH_3$ | 578 (M + H) |

What is claimed is:
1. A compound having the formula I:

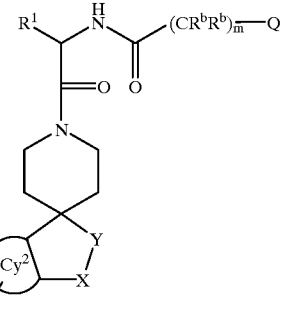

I wherein
Cy$^2$ is a six-membered aromatic ring containing 0 or 1N atom or cyclohexane;
Q is

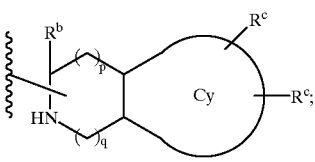

X is $CH_2$, $CHCO_2R^b$, $CHSO_2R^a$, $CHC(O)N(R^b)_2$, $NR^b$, $NSO_2R^a$, $NSO_2N(R^b)_2$, $NCOR^a$, $NCON(R^b)_2$, $CHN(R^b)COR^a$, $CHN(R^b)SO_2R^a$, $CHCH_2OR^b$, or $CH(CH_2)$-heteroaryl;

Y is $(CH_2)_r$, CH—$C_{1-8}$alkyl, or C=O;

$R^1$ is H, $C_{1-8}$alkyl, $CH(R^b)$-aryl, $CH(R^b)$-heteroaryl, $(CH_2)_n$—$C_{5-6}$cycloalkyl in which aryl and heteroaryl are optionally substituted by one or two $R^c$groups;

$R^2$ is H or halo;

$R^a$ is $R^b$, $(CH_2)_nN(R^b)_2$, $(CH_2)_nN(R^b)C(=NR^d)NR^b$, $(CH_2)_n$NH-2-pyridyl, $(CH_2)_n$NH-2-imidazolyl, $(CH_2)_n$NH-2-thiazolyl, $(CH_2)_n$NH-2-pyrimidinyl,

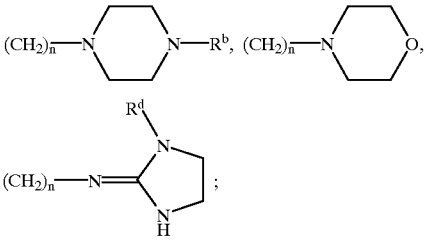

$R^b$ is H, $C_{1-8}$alkyl, $(CH_2)_n$aryl, $(CH_2)_n$heteroaryl, $C_{3-6}$cycloalkyl; or 2 $R^b$ together with the nitrogen atom to which they are attached form a 5- or 6-membered ring optionally containing an additional heteroatom selected from O, S, and $NR^1$;

$R^c$ is $R^b$, halo, $OR^b$, $NHSO_2R^b$, $N(R^b)_2$, CN, $NO_2$, $SO_2N(R^b)_2$, $SO_2R^b$, $CF_3$, $OCF_3$; or two $R^c$ groups attached to adjacent carbon atoms together form methylenedioxy;

$R^d$ is H, $NO_2$, or CN;

Cy is aryl or 5- or 6-membered carbocyclyl;

n is 0 to 3;

m, p and q are independently 0, 1 or 2;

r is 1, 2 or 3;

or a pharmaceutically acceptable salt thereof.

2. A compound of claim 1 wherein $Cy^2$ is benzene or cyclohexane.

3. A compound of claim 1 wherein X is $CHCO_2R^b$, $CHC(O)N(R^b)_2$, $NSO_2R^a$, $CHN(R^b)COR^a$, $CHN(R^b)SO_2R^a$, $CHCH_2OR^b$ or $CHCH_2$-heteroaryl.

4. A compound of claim 1 wherein Q is

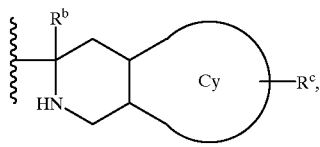

$R^b$ and $R^c$ are as defined in claim 1, and Cy is aryl or 5- or 6-membered carbocyclyl.

5. A compound of claim 1 wherein $R^1$ is $CH_2$-aryl in which aryl is optionally substituted by $R^c$.

6. A compound of claim 1 having the formula Ia:

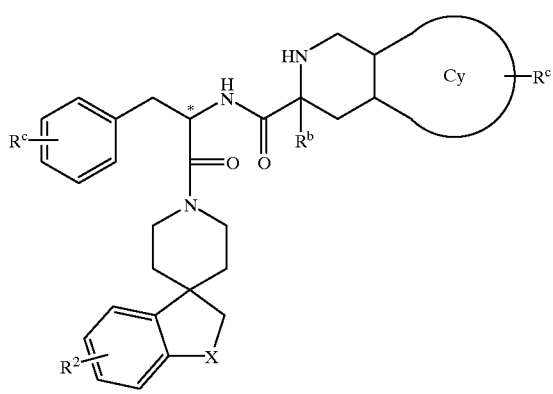

Ia wherein

X is $CHCO_2R^b$, $CHC(O)N(R^b)_2$, $NSO_2R^a$, $CHN(R^b)COR^a$, or $CHN(R^b)SO_2R^a$;

$R^2$ is H or halo;

$R^a$ is $R^b$, $(CH_2)_nN(R^b)_2$, $(CH_2)_n$NH-2-pyridyl, $(CH_2)_n$NH-2-imidazolyl, $(CH_2)_n$NH-2-thiazolyl, $(CH_2)_n$NH-2-pyrimidinyl,

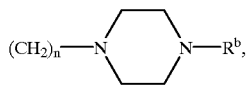

or

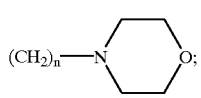

$R^b$ is H, $C_{1-8}$alkyl, $(CH_2)_n$aryl, $(CH_2)_n$heteroaryl, or $C_{3-6}$cycloalkyl;

$R^c$ is H, halo, $R^b$, $OR^b$, $CF_3$, $OCF_3$;

Cy is benzene or cyclohexane;

n is 0 to 3;

or a pharmaceutically acceptable salt thereof.

7. A compound of claim 6 wherein the carbon atom marked with * has the R configuration.

8. A compound of claim 7 wherein Cy is benzene or cyclohexane.

9. A compound of claim 1 having the formula Ib:

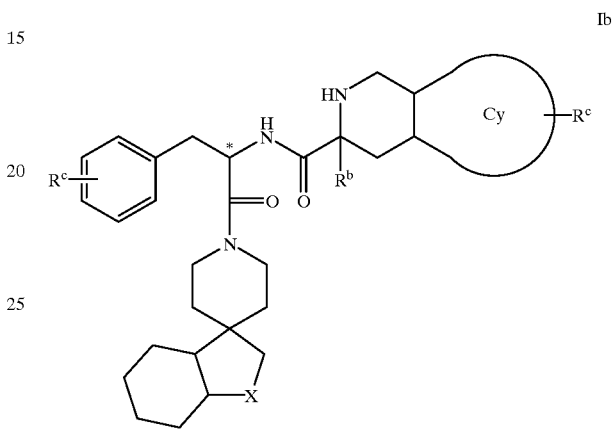

Ib wherein

X is $CHCO_2R^b$, $CHC(O)N(R^b)_2$, $CHCH_2OR^b$ or $CHCH_2$-heteroaryl;

$R^b$ is H, $C_{1-8}$alkyl, $(CH_2)_n$aryl, $(CH_2)_n$heteroaryl, or $C_{3-6}$cycloalkyl;

$R^c$ is H, halo, $R^b$, $OR^b$, $CF_3$, $OCF_3$;

Cy is benzene or cyclohexane;

n is 0 to 3;

or a pharmaceutically acceptable salt thereof.

10. A compound of claim 9 wherein the carbon atom marked with * has the R configuration.

11. A compound selected from the group consisting of:

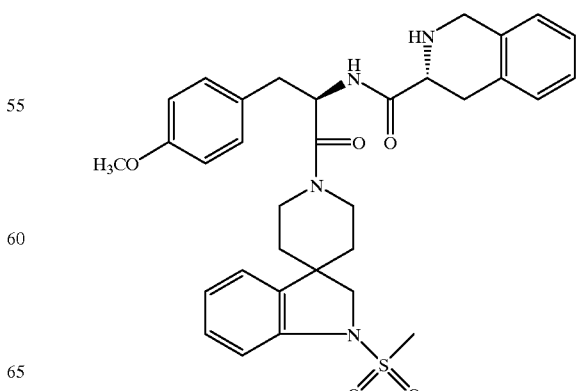

-continued
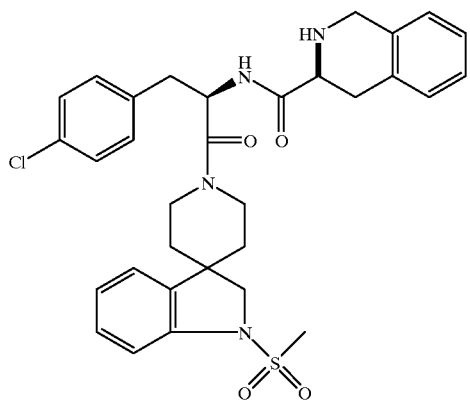
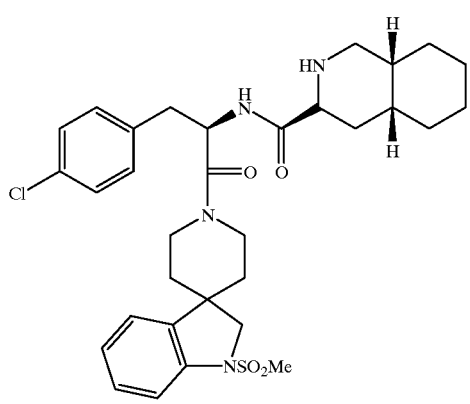
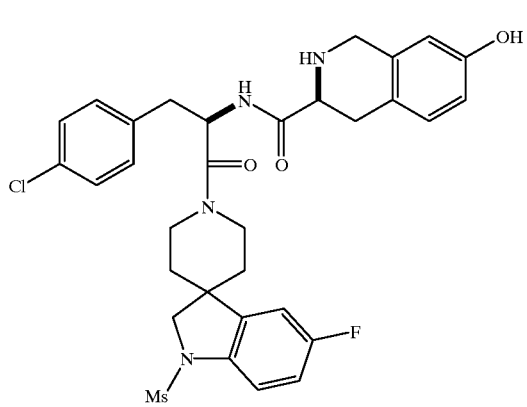
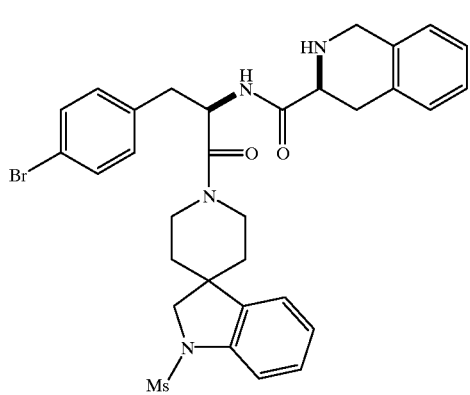
-continued
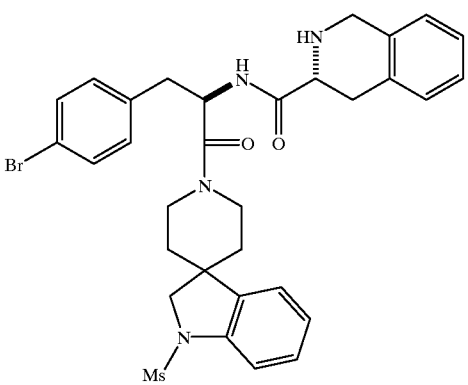
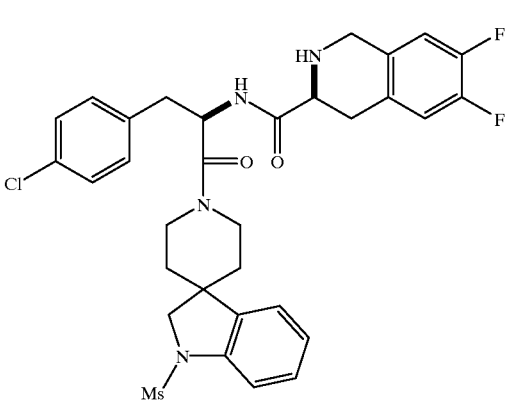
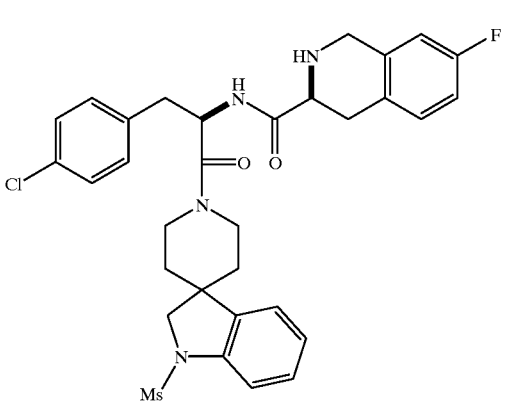
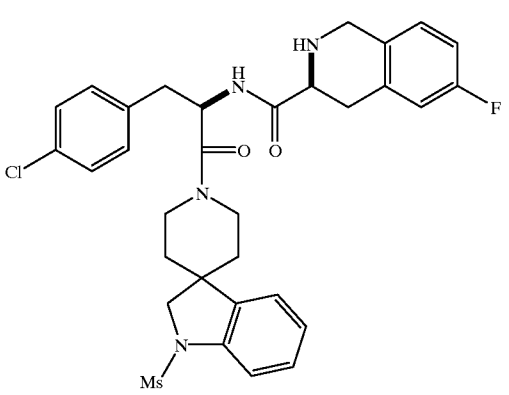

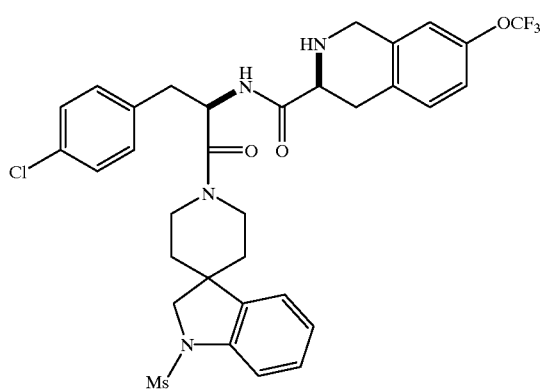

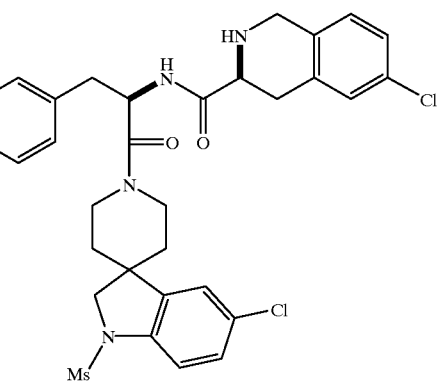

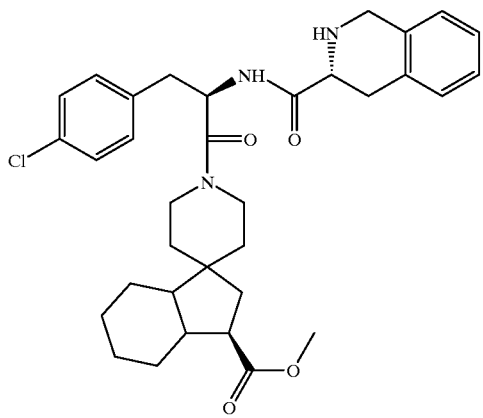

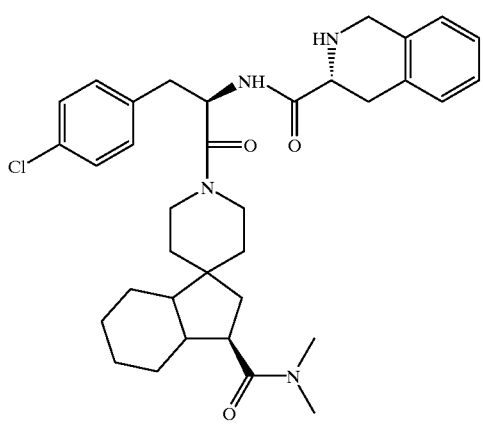

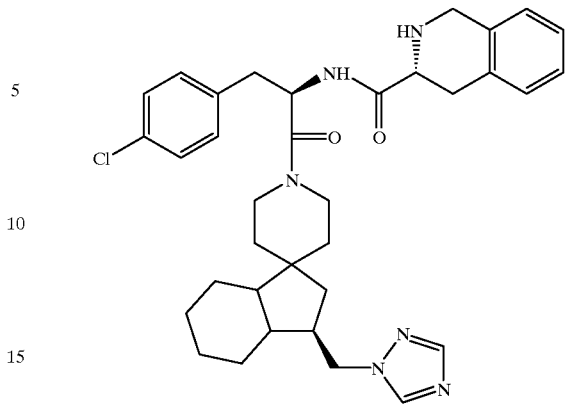

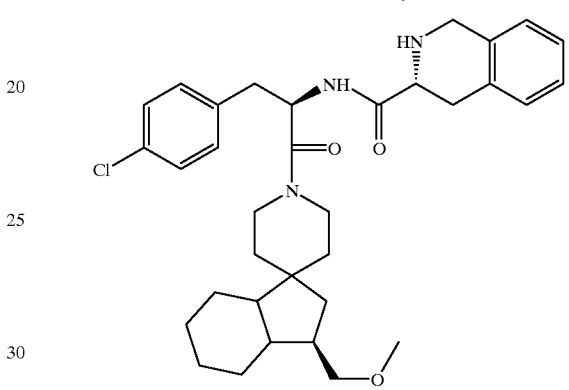

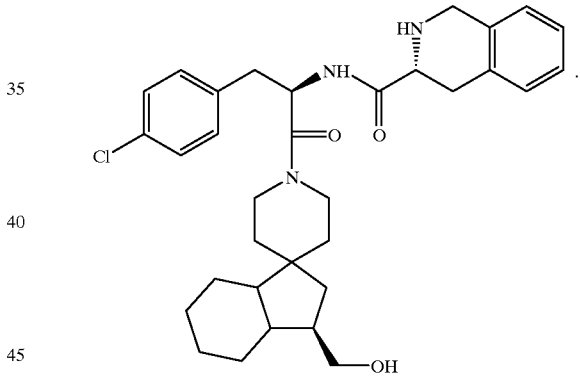

12. A method for the treatment of obesity which comprises administering to a mammal in need of such treatment an effective amount of a compound of claim 1.

13. A method for the treatment of diabetes mellitus which comprises administering to a mammal in need of such treatment an effective amount of a compound of claim 1.

14. A method for the treatment of male or female sexual dysfunction which comprises administering to a mammal in need of such treatment an effective amount of a compound of claim 1.

15. A method for the treatment of erectile dysfunction which comprises administering to a mammal in need of such treatment an effective amount of a compound of claim 1.

\* \* \* \* \*